United States Patent
Furutani et al.

(10) Patent No.: US 10,202,623 B2
(45) Date of Patent: Feb. 12, 2019

(54) RECOMBINANT CELL, AND METHOD FOR PRODUCING 1,4-BUTANEDIOL

(71) Applicant: SEKISUI CHEMICAL CO., LTD., Osaka (JP)

(72) Inventors: Masahiro Furutani, Tokyo (JP); Akihiro Uenishi, Tsukuba (JP); Koichiro Iwasa, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 583 days.

(21) Appl. No.: 14/760,793

(22) PCT Filed: Jan. 20, 2014

(86) PCT No.: PCT/JP2014/050998
§ 371 (c)(1),
(2) Date: Jul. 14, 2015

(87) PCT Pub. No.: WO2014/112627
PCT Pub. Date: Jul. 24, 2014

(65) Prior Publication Data
US 2015/0368677 A1 Dec. 24, 2015

(30) Foreign Application Priority Data
Jan. 21, 2013 (JP) .................................. 2013-008810

(51) Int. Cl.
| | | |
|---|---|---|
| C12N 1/20 | (2006.01) | |
| C12P 7/18 | (2006.01) | |
| C12N 9/10 | (2006.01) | |
| C12N 9/02 | (2006.01) | |
| C12N 9/88 | (2006.01) | |
| C12N 9/00 | (2006.01) | |
| C12N 9/04 | (2006.01) | |

(52) U.S. Cl.
CPC .............. *C12P 7/18* (2013.01); *C12N 9/0006* (2013.01); *C12N 9/0008* (2013.01); *C12N 9/10* (2013.01); *C12N 9/88* (2013.01); *C12N 9/93* (2013.01); *C12Y 101/01244* (2013.01); *C12Y 401/02043* (2013.01); *C12Y 402/03027* (2013.01)

(58) Field of Classification Search
None
See application file for complete search history.

(56) References Cited

U.S. PATENT DOCUMENTS

| | | | |
|---|---|---|---|
| 2006/0069040 A1* | 3/2006 | Mamelak ............... | A61K 31/19 514/23 |
| 2009/0075351 A1 | 3/2009 | Burk et al. | |
| 2010/0034453 A1 | 2/2010 | Lynch | |
| 2010/0218419 A1* | 9/2010 | Bai ........................... | C10L 5/36 44/589 |
| 2011/0129899 A1* | 6/2011 | Haselbeck ................ | C12P 7/18 435/243 |
| 2011/0146142 A1* | 6/2011 | Lee .......................... | C10L 1/026 44/388 |
| 2011/0190513 A1* | 8/2011 | Lynch ................... | C12N 9/0006 549/295 |
| 2011/0201071 A1* | 8/2011 | Burgard ............... | C12N 9/0006 435/158 |
| 2011/0203485 A1* | 8/2011 | Rahkola .................. | C01B 17/66 106/417 |
| 2012/0064622 A1* | 3/2012 | Fischer ..................... | C12P 5/00 435/348 |
| 2012/0208249 A1* | 8/2012 | Trawick ............... | C12N 9/0006 435/158 |
| 2014/0058056 A1 | 2/2014 | Burgard et al. | |

FOREIGN PATENT DOCUMENTS

| | | |
|---|---|---|
| JP | 2007-68424 | 3/2007 |
| JP | 2010-521182 | 6/2010 |
| JP | 2011-55722 | 3/2011 |
| JP | 2012-511928 | 5/2012 |
| WO | 2008/115840 | 9/2008 |
| WO | 2009/094485 | 7/2009 |
| WO | 2010/071697 | 6/2010 |
| WO | 2010/141920 | 12/2010 |
| WO | 2013/110797 | 8/2013 |
| WO | 2014/035925 | 3/2014 |

OTHER PUBLICATIONS

Yim et al. (2011) Metabolic engineering of *Escherichia coli* for direct production of 1,4-butanediol, Nature Chem. Biol., vol. 7, pp. 445-452.*
Supplementary European Search Report dated May 23, 2016 in European patent application No. 14 74 1160.
International Search Report dated Apr. 1, 2014 in International Application No. PCT/JP2014/050998.
International Preliminary Report on Patentability dated Jul. 21, 2015 in International (PCT) Application No. PCT/JP2014/050998.

\* cited by examiner

*Primary Examiner* — Manjunath N Rao
*Assistant Examiner* — Samuel W Liu
(74) *Attorney, Agent, or Firm* — Wenderoth, Lind & Ponack, L.L.P.

(57) ABSTRACT

An object of the present invention is to provide a series of techniques for producing 1,4-butanediol from methanol or the like. Provided is a recombinant cell prepared by introducing a gene encoding at least one enzyme selected from the group consisting of succinate semialdehyde dehydrogenase, succinyl-CoA synthase, CoA-dependent succinate semialdehyde dehydrogenase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell which is a methylotroph, wherein the gene is expressed in the host cell, and the recombinant cell is capable of producing 1,4-butanediol from at least one C1 compound selected from the group consisting of methane, methanol, methylamine, formic acid, formaldehyde, and formamide.

5 Claims, 2 Drawing Sheets

Specification includes a Sequence Listing.

(a) Succinyl-CoA synthetase (b) CoA-dependent succinate semialdehyde dehydrogenase (c) Succinate semialdehyde dehydrogenase (d) 2-oxoglutarate decarboxylase (e) 4-hydroxybutyrate dehydrogenase (f) 4-hydroxybutyryl-CoA transferase (g) 4-hydroxybutyryl-CoA reductase (h) Alcohol dehydrogenase (i) 4-hydroxybutyraldehyde dehydrogenase

RECOMBINANT CELL, AND METHOD FOR PRODUCING 1,4-BUTANEDIOL

TECHNICAL FIELD

The present invention relates to a recombinant cell capable of producing 1,4-butanediol from methanol or the like, and a method for producing 1,4-butanediol using the recombinant cell.

BACKGROUND ART 1,4-Butanediol is an organic compound that can be a raw material of butadiene which is important as a monomer of synthetic rubber, and is an important material, in particular, in the tire industry. In recent years, the technique for conversion from a production process of basic chemicals relying on petroleum to a production process from renewable resources such as plant resources has been developed and practical realization thereof is steadily progressing. Also regarding 1,4-butanediol, for example, a production technique from saccharides as a raw material by recombinant *Escherichia coli* is known (Patent Document 1).

The biosynthesis pathway of 1,4-butanediol is shown in FIG. 1. Specifically, 1,4-butanediol can be biosynthesized, for example, from succinate or α-ketoglutarate as a starting material.

In the pathway starting from succinate, succinate is converted into 1,4-butanediol via succinyl CoA, succinyl semialdehyde, 4-hydroxybutyrate, 4-hydroxybutyryl CoA, and 4-hydroxybutyraldehyde. Enzymes that catalyze these reactions are (a) succinyl-CoA synthase, (b) CoA-dependent succinate semialdehyde dehydrogenase, (e) 4-hydroxybutyrate dehydrogenase, (f) 4-hydroxybutyryl-CoA transferase, (g) 4-hydroxybutyryl-CoA reductase, and (h) alcohol dehydrogenase, respectively (FIG. 1). Every organism has (a) succinyl-CoA synthase.

Also, there is a pathway that directly converts succinate into succinyl semialdehyde. In that case, succinate is converted into 1,4-butanediol via succinyl semialdehyde, 4-hydroxybutyrate, 4-hydroxybutyryl CoA, and 4-hydroxybutyraldehyde. The enzyme that catalyzes the reaction of converting succinate into succinyl semialdehyde is (c) succinate semialdehyde dehydrogenase (FIG. 1).

On the other hand, in the pathway starting from α-ketoglutarate, α-ketoglutarate is converted into 1,4-butanediol via succinyl semialdehyde, 4-hydroxybutyrate, 4-hydroxybutyryl CoA, and 4-hydroxybutyraldehyde. The enzyme that catalyzes the reaction of converting α-ketoglutarate into succinyl semialdehyde is (d) 2-oxoglutarate decarboxylase (FIG. 1).

Further, there is a pathway that generates 4-hydroxybutyraldehyde directly from 4-hydroxybutyrate by (i) 4-hydroxybutyraldehyde dehydrogenase (FIG. 1).

Among C1 compounds, methanol is produced at a low cost from natural gas, synthetic gas which is a mixed gas of carbon monooxide, carbon dioxide and hydrogen obtained by incinerating waste such as biomass and municipal waste, and so on. Natural gas is focused as a next-generation energy source because it abundantly exists in fossil resources, and generates a relatively small amount of $CO_2$, and transition from conventional petroleum to natural gas is progressing. Methanol is easy to handle and stock because of its water solubility and so on, and is also suited as a carbon source in microbial culture.

A methylotroph is a general name for a C1 compound assimilating microorganism that uses a carbon compound not having a C—C bond in the molecule, e.g., methane, methanol, methylamine, dimethylamine, trimethylamine or the like as a sole carbon source or energy source. Any microorganisms called methanotroph, methane-oxidizing bacteria, methanol assimilating bacteria, methanol assimilating yeast, methanol assimilating microorganism belong to methylotrophs. Many bacterial methylotrophs are capable of assimilating methane, and these are often called methanotrophs.

Central metabolism of methylotroph is a reaction of converting formaldehyde into an organic matter having a C—C bond after converting methanol to formaldehyde. As shown in FIG. 2, as a carbon assimilation metabolism pathway via formaldehyde, a serine pathway, a ribulose monophosphate pathway (RuMP pathway), and a xylulose monophosphate pathway (XuMP pathway) can be recited. Methylotrophs classified into bacteria (methylotrophic bacteria) have a serine pathway or a RuMP pathway. On the other hand, methylotrophs classified into yeast (methylotrophic yeast) has a XuMP pathway.

Methylotrophic bacteria are classified into obligate methylotrophs and facultative methylotrophs capable of using other carbon compound according to the difference in methanol requirement.

PRIOR ART DOCUMENTS

Patent Document

Patent Document 1: WO 2010/141920

DISCLOSURE OF INVENTION

Technical Problem

Regarding the production process from renewable resources, most of the conventional techniques including the aforementioned 1,4-butanediol production technique are production methods by microorganisms relying on organic substances, in particular, saccharides, glycerol or oil components. However, for covering the global production quantity of a large number of basic chemicals derived from petroleum, the amounts of currently available saccharides, glycerin and oil components derived from plant resources and the like will be necessarily insufficient for carbon sources of microorganisms. In other words, the production amounts of basic chemicals by microorganisms relying on saccharides or oil components is limited also in the future. These processes also have a fear of competition with foods.

In light of the above, it is an object of the present invention to provide a series of techniques capable of producing 1,4-butanediol from methanol or the like.

Solution to Problem

One aspect of the present invention for solving the aforementioned problem is a recombinant cell prepared by introducing a gene encoding at least one enzyme selected from the group consisting of succinate semialdehyde dehydrogenase, succinyl-CoA synthase, CoA-dependent succinate semialdehyde dehydrogenase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell which is a methylotroph, wherein the gene is expressed in the host cell, and the recombinant cell is capable of producing 1,4-butanediol from at least one C1 compound selected from the group consisting of methane, methanol, methylamine, formic acid, formaldehyde, and formamide.

As illustrated in FIG. 1, 1,4-butanediol can be biosynthesized from succinate. The recombinant cell of the present invention is prepared by introducing a gene encoding at least one enzyme selected from the group of enzymes acting in a biosynthesis pathway from succinate to 1,4-butanediol, namely the group consisting of succinate semialdehyde dehydrogenase, succinyl-CoA synthase, CoA-dependent succinate semialdehyde dehydrogenase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell which is a methylotroph, wherein the gene is expressed in the host cell. And it is able to produce 1,4-butanediol from at least one C1 compound selected from the group consisting of methane, methanol, methylamine, formic acid, formaldehyde, and formamide.

According to the recombinant cell of the present invention, it is possible to produce 1,4-butanediol from the aforementioned C1 compound via succinate based on "the function of converting methanol and/or formic acid into formaldehyde" and "formaldehyde fixing ability" that are inherent in a methylotroph.

Another aspect of the present invention for solving a similar problem is a recombinant cell prepared by introducing a gene encoding at least one enzyme selected from the group consisting of 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell which is a methylotroph, wherein the gene is expressed in the host cell, and the recombinant cell is capable of producing 1,4-butanediol from at least one C1 compound selected from the group consisting of methane, methanol, methylamine, formic acid, formaldehyde, and formamide.

As illustrated in FIG. 1, 1,4-butanediol can be biosynthesized also from α-ketoglutarate. And the recombinant cell of the present invention is prepared by introducing a gene encoding at least one enzyme selected from the group of enzymes acting in a biosynthesis pathway from α-ketoglutarate to 1,4-butanediol, namely the group consisting of 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell which is a methylotroph, wherein the gene is expressed in the host cell. And it is able to produce 1,4-butanediol from at least one C1 compound selected from the group consisting of methane, methanol, methylamine, formic acid, formaldehyde, and formamide.

According to the recombinant cell of the present invention, it is possible to produce 1,4-butanediol from the C1 compound via α-ketoglutarate based on "the function of converting methanol and/or formic acid into formaldehyde" and "formaldehyde fixing ability" that are inherent in a methylotroph.

Preferably, the recombinant cell has at least one C1 carbon assimilating pathway selected from the group consisting of a serine pathway, a ribulose monophosphate pathway, and a xylulose monophosphate pathway as a fixing pathway of formaldehyde.

Preferably, a gene encoding 3-hexulose-6-phosphate synthase and a gene encoding 6-phospho-3-hexuloisomerase are further introduced, and the genes are expressed in the host cell.

With such a configuration, formaldehyde fixing ability by the ribulose monophosphate pathway is imparted or enhanced.

Preferably, the host cell is methanol assimilating yeast, and a gene encoding an enzyme that converts methanol into formaldehyde by dehydrogenation is further introduced, and the gene is expressed in the host cell.

In general, yeast is highly tolerant to alcohol. In light of this, the present aspect employs methanol assimilating yeast as a host cell, and enhances the tolerance of the recombinant cell to 1,4-butanediol. Further, in yeast, generally, alcohol oxydase is responsible for conversion from methanol to formaldehyde. For this reason, oxygen is required for the conversion reaction, and concretely, vigorous aeration is required during cultivation. Therefore, in this aspect, a gene encoding "enzyme that converts methanol into formaldehyde by dehydrogenation" is introduced so that conversion from methanol to formaldehyde is conducted without relying on oxygen.

Another aspect of the present invention for solving a similar problem is a recombinant cell prepared by introducing a gene imparting the function of converting methanol and/or formic acid into formaldehyde, a gene imparting formaldehyde fixing ability, and a gene encoding at least one enzyme selected from the group consisting of succinate semialdehyde dehydrogenase, succinyl-CoA synthase, CoA-dependent succinate semialdehyde dehydrogenase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell, and the genes are expressed in the host cell, and the recombinant cell is capable of producing 1,4-butanediol from at least one C1 compound selected from the group consisting of methane, methanol, methylamine, formic acid, formaldehyde, and formamide.

The recombinant cell of the present invention is prepared by introducing a "gene imparting the function of converting methanol and/or formic acid into formaldehyde" and a "gene imparting formaldehyde fixing ability" and further introducing a gene encoding at least one enzyme selected from the group of enzymes acting in a biosynthesis pathway from succinate to 1,4-butanediol, namely the group consisting of succinate semialdehyde dehydrogenase, succinyl-CoA synthase, CoA-dependent succinate semialdehyde dehydrogenase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase into a host cell. And it is able to produce 1,4-butanediol from at least one C1 compound selected from the group consisting of methane, methanol, methylamine, formic acid, formaldehyde, and formamide.

That is, since the recombinant cell of the present invention is prepared by introducing a "gene imparting the function of converting methanol and/or formic acid into formaldehyde" and a "gene imparting formaldehyde fixing ability", it has characteristics similar to those of methylotroph. Based on the "function of converting methanol and/or formic acid into formaldehyde" and the "formaldehyde fixing ability" imparted by these foreign genes, it can produce 1,4-butanediol from the C1 compound via succinate.

Another aspect of the present invention for solving a similar problem is a recombinant cell prepared by introducing a gene imparting the function of converting methanol and/or formic acid into formaldehyde, a gene imparting formaldehyde fixing ability, and a gene encoding at least one enzyme selected from the group consisting of 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase into a host cell, wherein the genes are expressed in the host cell, and the recombinant cell is capable of producing 1,4-butanediol from at least one C1 compound selected from the group consisting of methane, methanol, methylamine, formic acid, formaldehyde, and formamide.

The recombinant cell of the present invention is prepared by introducing a "gene imparting the function of converting methanol and/or formic acid into formaldehyde" and a "gene imparting formaldehyde fixing ability", and a gene encoding at least one enzyme selected from the group of enzymes acting in a biosynthesis pathway from α-ketoglutarate to 1,4-butanediol, namely the group consisting of 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell. And it is able to produce 1,4-butanediol from at least one C1 compound selected from the group consisting of methane, methanol, methylamine, formic acid, formaldehyde, and formamide.

That is, since the recombinant cell of the present invention is prepared by introducing a "gene imparting the function of converting methanol and/or formic acid into formaldehyde" and a "gene imparting formaldehyde fixing ability", it has characteristics similar to those of methylotroph. And based on the "function of converting methanol and/or formic acid into formaldehyde" and the "formaldehyde fixing ability" imparted by these foreign genes, it can produce 1,4-butanediol from the C1 compound via α-oxoglutarate.

Preferably, the gene imparting formaldehyde fixing ability is a gene encoding 3-hexulose-6-phosphate synthase and a gene encoding 6-phospho-3-hexuloisomerase.

With such a configuration, formaldehyde fixing ability by the ribulose monophosphate pathway is imparted.

Preferably, it has at least one C1 carbon assimilating pathway selected from the group consisting of a serine pathway, a ribulose monophosphate pathway, and a xylulose monophosphate pathway as a fixing pathway of formaldehyde.

Another aspect of the present invention for solving a similar problem is a recombinant cell prepared by introducing a gene imparting the function of converting methanol and/or formic acid into formaldehyde, and a gene encoding at least one enzyme selected from the group consisting of succinate semialdehyde dehydrogenase, succinyl-CoA synthase, CoA-dependent succinate semialdehyde dehydrogenase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell having a ribulose monophosphate pathway, wherein the genes are expressed in the host cell, and the recombinant cell is capable of producing 1,4-butanediol from at least one C1 compound selected from the group consisting of methane, methanol, methylamine, formic acid, formaldehyde, and formamide.

Another aspect of the present invention for solving a similar problem is a recombinant cell prepared by introducing a gene imparting the function of converting methanol and/or formic acid into formaldehyde, and a gene encoding at least one enzyme selected from the group consisting of 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase, into a host cell having a ribulose monophosphate pathway, wherein the genes are expressed in the host cell, and the recombinant cell is capable of producing 1,4-butanediol from at least one C1 compound selected from the group consisting of methane, methanol, methylamine, formic acid, formaldehyde, and formamide.

These aspects correspond to the form in which, for example, a non-methylotroph having a ribulose monophosphate pathway is a host cell.

Preferably, a gene encoding 3-hexulose-6-phosphate synthase and a gene encoding 6-phospho-3-hexuloisomerase are further introduced, and the genes are expressed in the host cell.

Preferably, the gene imparting the function of converting methanol into formaldehyde is a gene encoding methanol dehydrogenase or alcohol oxydase, and the gene imparting the function of converting formic acid into formaldehyde is a gene encoding formaldehyde dehydrogenase.

Both of methanol dehydrogenase and alcohol dehydrogenase have the function of converting methanol into formaldehyde. Also, formaldehyde dehydrogenase has the function of converting formic acid into formaldehyde. Any of these enzymes is one of methane metabolism enzymes in methylotrophs belonging to bacteria. On the other hand, methylotrophs belonging to yeast do not have methane oxidizing activity, but have the function of converting methanol into formaldehyde by the action of alcohol oxydase. Also yeast has the enzymatic activity of converting formic acid into formaldehyde.

Preferably, a gene imparting the function of converting methane into methanol is further introduced, and the gene is expressed in the host cell.

Preferably, the gene imparting the function of converting methane into methanol is a gene encoding methane monooxygenase.

Methane monooxygenase has the function of converting methane into methanol. Also methane monooxygenase is one of methane metabolism enzymes in methylotroph.

Preferably, the introduced gene is incorporated in a genome of the host cell.

With such a configuration, the introduced gene is retained in the recombinant cell more stably.

Preferably, the introduced gene is incorporated in a plasmid.

Preferably, it is tolerant to at least 400 mM 1,4-butanediol.

With such a configuration, a larger amount of 1,4-butanediol can be produced.

Preferably, it is tolerant to at least 2% (v/v) methanol.

With such a configuration, a larger amount of 1,4-butanediol can be produced.

Another aspect of the present invention is a method for producing 1,4-butanediol, including culturing the aforementioned recombinant cell by using at least one C1 compound selected from the group consisting of methane, methanol, methylamine, formic acid, formaldehyde, and formamide as a carbon source, to cause the recombinant cell to produce 1,4-butanediol.

The present invention relates to a method for producing 1,4-butanediol. In the present invention, by culturing the recombinant cell by using at least one C1 compound selected from the group consisting of methane, methanol, methylamine, formic acid, formaldehyde, and formamide as a carbon source, the recombinant cell is caused to produce 1,4-butanediol. According to the present invention, it is possible to produce 1,4-butanediol from methanol or the like.

Another aspect of the present invention is a method for producing 1,4-butanediol, including bringing at least one C1 compound selected from the group consisting of methane, methanol, methylamine, formic acid, formaldehyde, and formamide into contact with the aforementioned recombinant cell, to cause the recombinant cell to produce 1,4-butanediol from the C1 compound.

In the present invention, by bringing at least one C1 compound selected from the group consisting of methane, methanol, methylamine, formic acid, formaldehyde, and formamide into contact with the aforementioned recombinant cell, the recombinant cell is caused to produce 1,4-butanediol from the C1 compound. Also with the present invention, it possible to produce 1,4-butanediol from methanol or the like.

Advantageous Effect of Invention

According to the recombinant cell of the present invention, it is possible to produce 1,4-butanediol from methane, methanol, methylamine, formic acid, formaldehyde, or formamide.

Similarly, according to the method for producing 1,4-butanediol of the present invention, it is possible to produce 1,4-butanediol from methane, methanol, methylamine, formic acid, formaldehyde, or formamide.

DESCRIPTION OF EMBODIMENT

Hereinafter, embodiments of the present invention will be described. In the present invention, the term "gene" can be replaced by the term "nucleic acid" or "DNA".

The recombinant cell of the present invention is basically prepared by introducing a gene encoding a group of enzymes acting in the biosynthesis pathway from succinate or α-ketoglutarate to 1,4-butanediol into a host cell having "function of converting methanol and/or formic acid into formaldehyde" and "formaldehyde fixing ability".

The host cell employed in the present invention may be any of methylotrophic host cells, and a wide range of host cells including a non-methylotroph.

As described above, a methylotroph is a C1 compound assimilating microorganism that uses a carbon compound not having a C—C bond in the molecule, e.g., methane, methanol, methylamine, dimethylamine, trimethylamine or the like as a sole carbon source or energy source. In general, a methylotroph originally has a carbon assimilation metabolism pathway via formaldehyde, concretely the function (pathway) of converting methanol and/or formic acid to formaldehyde, and a formaldehyde fixing ability (fixing pathway of formaldehyde).

Figure 2:
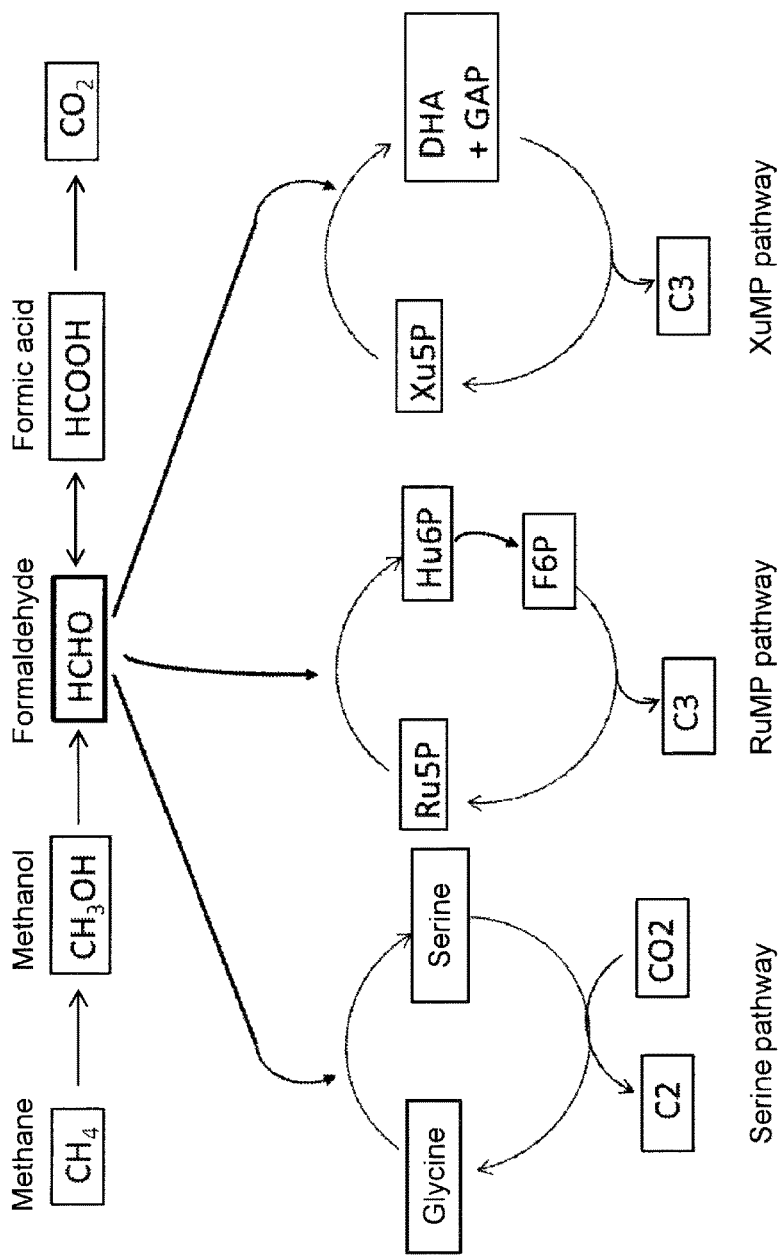
FIG. 2 is an explanatory diagram showing a carbon assimilating metabolic pathway via formaldehyde.

As a fixing pathway of formaldehyde, a serine pathway, a ribulose monophosphate pathway (RuMP pathway), and a xylulose monophosphate pathway (XuMP pathway) shown in FIG. 2 can be recited. In general, a methylotroph has a serine pathway, a RuMP pathway, or a XuMP pathway as a carbon assimilation metabolism pathway via formaldehyde.

Here, description will be made for each formaldehyde fixing pathway (FIG. 2).

The important reaction for formaldehyde fixation by the serine pathway is serine generation reaction of glycine and 5,10-methylene-tetrahydrofolic acid by serine hydroxymethyltransferase. Generation of 5,10-methylene-tetrahydrofolic acid is made by binding formaldehyde to tetrahydrofolic acid. In the serine pathway, one molecule of acetyl CoA is directly generated from one molecule of formaldehyde.

The important reactions for formaldehyde fixation by the RuMP pathway are generation reaction of D-arabino-3-hexulose-6-phosphate from ribulose 5-phosphate (Ru5P) and formaldehyde by 3-hexulose-6-phosphate synthase (hereinafter, also abbreviated as "HPS"), and generation reaction of fructose-6-phosphate (F6P) from D-arabino-3-hexulose-6-phosphate by 6-phosphate-3-hexuloisomerase (hereinafter, also abbreviated as "PHI").

F6P and the like generated in this pathway are also supplied to a glycolytic pathway to subsequently generate acetyl CoA, glyceraldehyde 3-phosaphate (G3P) and pyruvic acid. In the case of F6P, one molecule of F6P is converted to two molecules of G3P, and then two molecules of acetyl CoA are generated via two molecules of pyruvic acid.

The important reaction for formaldehyde fixation by the XuMP pathway is generation reaction of dihydroxyacetone (DHA) and glyceraldehyde-3-phosphate (G3P) from xylulose-5-phosphate (Xu5P) and formaldehyde by dihydroxyacetone synthase. G3P generated in this pathway is also supplied to the glycolytic pathway, and converted to pyruvic acid and acetyl CoA. Dihydroxyacetone is also supplied to the glycolytic pathway by phosphorylation, and can be converted to G3P, pyruvic acid, and acetyl CoA.

The recombinant cell of the present invention is capable of producing 1,4-butanediol from at least one C1 compound selected from the group consisting of methane, methanol, methylamine, formic acid, formaldehyde, and formamide. For example, a recombinant cell having methanol dehydrogenase or alcohol oxydase is able to convert methanol to formaldehyde.

A recombinant cell having methane monooxydase in addition to methanol dehydrogenase or alcohol oxydase is able to convert methane to methanol, and then convert methanol to formaldehyde.

Further, a recombinant cell having formaldehyde dehydrogenase is able to convert formic acid to formaldehyde.

In general, methylotrophs classified into bacteria (methylotrophic bacteria) are able to synthesize formaldehyde from methane or methanol because they have methane monooxygenase and methanol dehydrogenase. Further, methylotrophs classified into yeast (methylotrophic yeast) are able to synthesize formaldehyde from methanol because they have alcohol oxydase. Further, methylotrophs have formaldehyde dehydrogenase, and are able to convert formic acid to formaldehyde.

The aforementioned methanol dehydrogenase includes pyrroloquinoline quinone (PQQ)-dependent methanol dehydrogenase found in methylotrophs of gram negative bacteria, NAD(P)-dependent methanol dehydrogenase and alcohol dehydrogenase found in methylotrophs of gram positive bacteria, and N,N'-dimethyl-4-nitrosoaniline (DMNA)-dependent methanol oxide reductase (Park H. et al., Microbiology 2010, 156, 463-471) found in methylotrophs of gram positive bacteria. The conversion from methanol to formaldehyde in yeast is usually catalyzed by oxygen-dependent alcohol oxydase.

Also a recombinant cell having amine oxidase or a methylamine dehydrogenase is able to convert methylamine to formaldehyde. These enzymes are known to be inherent in some methylotrophs and Arthrobacter bacteria (Anthony C., The Biochemistry of Methylotroph, 1982, Academic Press Inc.)

Also, enzymes that convert formamide to formaldehyde are found in some microorganisms (Anthony C., The Biochemistry of Methylotroph, 1982, Academic Press Inc.)

Additionally, 1,4-butanediol can be produced via formaldehyde.

While the kind of methylotrophs to be used as a host cell is not particularly limited, for example, those classified into bacteria or yeast can be employed.

Examples of methylotrophic bacteria include bacteria belonging to genus *Methylacidphilum*, genus *Methylosinus*, genus *Methylocystis*, genus *Methylobacterium*, genus *Methylocella*, genus *Methylococcus*, genus *Methylomonas*, genus *Methylobacter*, genus *Methylobacillus*, genus *Methylophilus*, genus *Methylotenera*, genus *Methylovorus*, genus *Methylomicrobium*, genus *Methylophaga*, genus *Methylophilaceae*, genus *Methyloversatilis*, genus *Mycobacterium*, genus *Arthrobacter*, genus *Bacillus*, genus *Beggiatoa*, genus *Burkholderia*, genus *Granulibacter*, genus *Hyphomicrobium*, genus *Pseudomonas*, genus *Achromobactor*, genus *Paracoccus*, genus *Crenothrix*, genus *Clonothrix*, genus *Rhodobacter*, genus *Rhodocyclaceae*, genus *Silicibacter*, genus *Thiomicrospira*, and genus *Verrucomicrobia*.

Examples of methylotrophic yeasts include yeast belonging to genus *Pichia*, genus *Candida*, genus *Saccharomyces*, genus *Hansenula*, genus *Torulopsis*, and genus *Kloeckera*. Examples of *Pichia* yeasts include *P. haplophila*, *P. pastoris*, *P. trehalophila*, and *P. lindnerii*. Examples of *Candida* yeasts include *C. parapsilosis*, *C. methanolica*, *C. boidinii*, and *C. alcomigas*. Example of *Saccharomyces* yeast includes *Saccharomyces* metha-nonfoams. Examples of *Hansenula* yeasts include *H. wickerhamii*, *H. capsulata*, *H. glucozyma*, *H. henricii*, *H. minuta*, *H. nonfermentans*, *H. philodendra*, and *H. polymorpha*. Examples of *Torulopsis* yeasts include *T. methanolovescens*, *T. glabrata*, *T. nemodendra*, *T. pinus*, *T. methanofloat*, *T. enokii*, *T. menthanophiles*, *T. methanosorbosa*, and *T. methanodomercqii*.

When the host cell is a non-methylotroph, it is necessary to impart at least "the function of converting methanol and/or formic acid to formaldehyde" because the host cell does not always have a pathway of converting methanol or the like to formaldehyde. Further, it is preferred to impart "the function of converting methane to methanol". Impartation of such functions can be achieved by introducing a gene encoding the aforementioned enzyme into the host cell.

For example, as a gene imparting the function of converting methanol to formaldehyde, a gene encoding methanol dehydrogenase (for example, EC1.1.1.244, EC1.1.2.7) or a gene encoding alcohol oxydase (for example, EC1.13.13) can be used. As a gene imparting the function of converting formic acid to formaldehyde, a gene encoding formaldehyde dehydrogenase (e.g., EC1.2.1.46) can be used. Further, as a gene imparting the function of converting methane to methanol, a gene encoding methane monooxygenase can be used.

Also a plasmid imparting methanol assimilability is known. For example, methanol assimilability of *Bacillus methanolicus* relies on a plasmid encoding a group of enzymes involved in methanol metabolism (Brautaset T. et al., J. Bacteriology 2004, 186(5), 1229-1238). By introducing such a plasmid to a related non-methylotroph, it is possible to impart methanol assimilability. Further, by modifying such a plasmid, it is possible to impart methanol assimilability to various non-methylotrophs.

In the manner as described above, by imparting "the function of converting methanol and/or formic acid to formaldehyde", and further imparting "the formaldehyde fixing ability" to a non-methylotroph, it becomes possible to handle a non-methylotroph similarly to a methylotroph. Impartation of the formaldehyde fixing ability can be realized, for example, by introducing a gene encoding an enzyme acting in the serine pathway, RuMP pathway, or XuMP pathway into a non-methylotroph.

In one preferred embodiment, the host cell is methanol assimilating yeast, an enzyme that converts methanol into formaldehyde by dehydrogenation is further introduced, and the gene is expressed in the host cell. For example, by using *Pichia* yeast having methanol assimilability as a host cell, and further introducing methanol dehydrogenase gene, it is possible to acquire a desired recombinant cell. According to the present embodiment, it is possible to obtain a recombinant cell capable of producing 1,4-butanediol, that is highly tolerant to alcohol, and is capable of converting methanol to formaldehyde without relying on oxygen.

Further description will be made while taking the case of imparting the RuMP pathway as an example. Impartation of the RuMP pathway can be realized, for example, by introducing the aforementioned 3-hexulose-6-phosphate synthase (HPS; e.g., EC4.1.2.43) gene and a 6-phospho-3-hexuloisomerase (PHI; e.g., EC5.3.1.27) gene. That is, ribulose 5-phosphate (Ru5P) and fluctose 6-phosphate (F6P) which are a substrate or a product of the formaldehyde fixing reaction by HPS/PHI generally exist in any organism as metabolic intermediates of the pentose phosphate pathway, and the calvin cycle. Therefore, by introducing HPS/PHI, it is possible to impart the formaldehyde fixing ability to every organism including *Escherichia coli*, *Bacillus subtilis*, and yeast.

A HPS gene and a PHI gene may be introduced to a host cell originally having the RuMP pathway. As a result, it is possible to enhance the formaldehyde fixing ability by the RuMP pathway. For example, by introducing genes encoding enzymes such as alcohol dehydrogenase such as methanol dehydrogenase (e.g., EC1.1.1.244, EC1.1.2.7), 3-hexulose 6-phosphate synthase (HPS; e.g., EC4.1.2.43), 6-phospho-3-hexuloisomerase (PHI; e.g., EC5.3.1.27) to a microorganism originally having the RuMP pathway or a pathway equivalent to the same, such as *Bacillus subtilis*, it is possible to impart the function of converting methanol to formaldehyde (i.e. methanol assimilability) and to enhance the formaldehyde fixing ability.

HPS gene and PHI gene may be introduced into a host cell which is a methylotroph. That is, by introducing HPS/PHI to a methylotroph having a serine pathway, a RuMP pathway, or a XuMP pathway, it is possible to enhance the formaldehyde fixing ability by the RuMP pathway. As a result, it is possible to improve the formaldehyde resistance of the recombinant cell, and to improve the resistance and assimilability to methanol and formic acid. As a result, it becomes possible to increase the culture efficiency of the recombinant cell and the production efficiency of 1,4-butanediol.

On the other hand, for imparting the formaldehyde fixing ability by the serine pathway, the aforementioned serine hydroxymethyl transferase (e.g., EC2.1.2.1) gene can be employed. For example, by introducing alcohol dehydrogenase (e.g. methanol dehydrogenase) gene, 5,10-methylenetetrahydrofolate ($CH_2=H4F$) synthase gene, and serine hydroxymethyltransferase (e.g., EC2.1.2.1) gene into a non-methylotroph, it is possible to impart the formaldehyde fixing ability by the methanol assimilability and the serine pathway.

Figure 1:
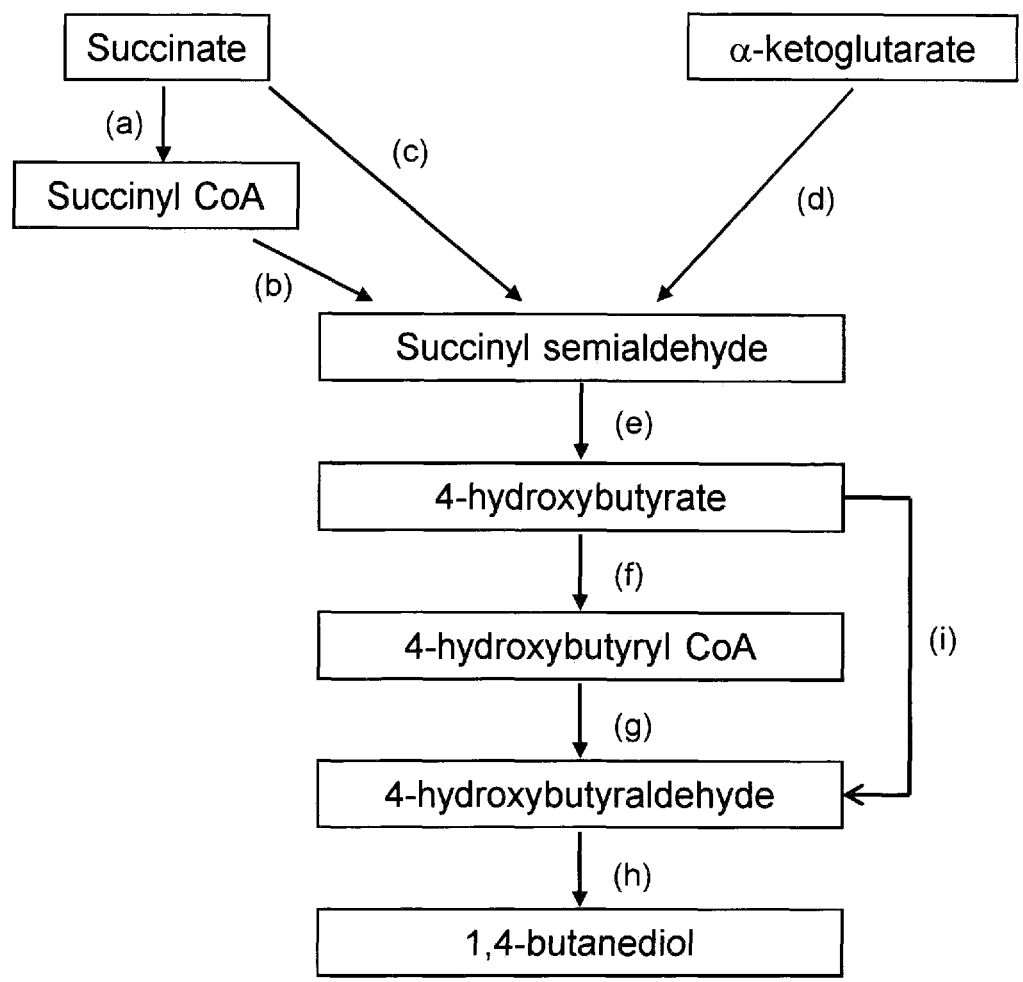
FIG. 1 is an explanatory diagram showing a metabolic pathway from succinate or α-ketoglutarate to 1,4-butanediol.

In the recombinant cell of the present invention, a gene encoding a group of enzymes acting in the biosynthesis pathway from succinate or α-ketoglutarate to 1,4-butanediol (hereinafter, collectively called "1,4-butanediol biosynthesis related enzyme(s)") is introduced. The enzymes represented by (a) to (i) of FIG. 1 correspond to the 1,4-butanediol biosynthesis related enzymes.

In one aspect, a gene encoding at least one enzyme selected from the group consisting of (c) succinate semialdehyde dehydrogenase, (a) succinyl-CoA synthase, (b) CoA-dependent succinate semialdehyde dehydrogenase, (e) 4-hydroxybutyrate dehydrogenase, (f) 4-hydroxybutyryl-CoA transferase, (g) 4-hydroxybutyryl-CoA reductase, (i) 4-hydroxybutyraldehyde dehydrogenase, and (h) alcohol dehydrogenase as a group of enzymes acting in the biosynthesis pathway from succinate to 1,4-butanediol is introduced in a host cell. For example, one or more enzymes can be selected from the group of enzymes, and a gene encoding the enzyme can be introduced into the host cell.

In another aspect, as a group of enzymes acting in the biosynthesis pathway from α-ketoglutarate to 1,4-butanediol, a gene encoding at least one enzyme selected from the group consisting of (d) 2-oxoglutarate decarboxylase, (e) 4-hydroxybutyrate dehydrogenase, (f) 4-hydroxybutyryl-CoA transferase, (g) 4-hydroxybutyryl-CoA reductase, (i) 4-hydroxybutyraldehyde dehydrogenase, and (h) alcohol dehydrogenase is introduced into a host cell. For example, one or more enzymes can be selected from the group of enzymes, and a gene encoding the enzyme can be introduced into the host cell.

These enzymes (1,4-butanediol biosynthesis related enzymes) are not particularly limited as far as they can exert the enzymatic activity in the recombinant cell. Similarly, the genes encoding these enzymes are not particularly limited as far as they are normally transcribed and translated in the recombinant cell. They may be derived from the host cell, or from others.

Concrete examples of 1,4-butanediol biosynthesis related enzymes and genes thereof include those disclosed in Patent Document 1. For example, the following enzymes can be recited. When the host cell originally has the enzyme shown below, a gene of enzyme having higher substrate specificity, molecular activity and stability, namely having a higher value of Kcat/Km can be introduced. In this case, the enzyme gene includes a gene encoding a modified enzyme of the enzyme that is inherent in the host cell. Optimization or avoidance of low frequency of codons of the introduced gene can be achieved in individual host microorganisms by referring to "Codon Usage Database" (http://www.kazusa.or.jp/codon/).

(c) Succinate semialdehyde dehydrogenase (e.g., EC 1.2.1.16, EC 1.2.1.24)

Examples of genes include (each indicated by UniProtKB No.) P76149 (*E. coli*); P25526 (*E. coli*); P94428 (*Bacillus subtilis*); Q55585 (*Synechocystis* sp.); and P38067 (*Saccharomyces cerevisiae*).

(a) Succinyl-CoA synthase (Succinyl-CoA synthetase, Succinyl-CoA ligase: e.g., EC 6.2.1.4, EC 6.2.1.5 etc.)

Examples of genes include (each indicated by UniProtKB/Swiss-Prot No.) P0AGE9 (*E. coli*); P0A836 (*E. coli*); P53598 (*Saccharomyces cerevisiae*); P53312 (*Saccharomyces cerevisiae*); P09143 (*Thermus thermophilus*); and O82662 (*Arabidopsis thaliana*). The present enzymatic activity is possessed by every organism, however, it is also effective to introduce the enzymatic activity as a foreign gene as is necessary.

(b) CoA-dependent succinate semialdehyde dehydrogenase (e.g., EC 1.2.1.79)

Examples of genes include (each indicated by UniProtKB/Swiss-Prot No.) P38947 (*Clostridium kluyveri*); A4YGN0 (*Metallosphaera sedula*) etc.

(e) 4-hydroxybutyrate dehydrogenase (e.g., EC 1.1.1.61) Examples of genes include (each indicated by UniProtKB/Swiss-Prot No.) D8GUP1 (*Clostridium ljungdahlii*); C9YNR6 (*Clostridium difficile*); Q97IR6 (*Clostridium acetobutylicum*); Q8XYI7 (*Ralstonia solanacearum*); Q7MWD4 (*Porphyromonas gingivalis*) etc.

(f) 4-hydroxybutyryl-CoA transferase (e.g., EC2.8.3.a)

Examples of genes include (each indicated by UniProtKB/Swiss-Prot No.) Q9RM86 (*Clostridium aminobutyricum*); P38942 (*Clostridium kluyveri*); Q185L2 (*Clostridium difficile*); Q3ACH6 (*Carboxydothermus hydrogenoformas*); C4Z8H6 (*Eubacterium rectale*); I8UF15 (*Porphyromonas gingivalis*) etc.

(g) 4-hydroxybutyryl-CoAreductase (e.g., EC1.2.1.10 etc., 4-hydroxybutyryl-CoA reductase activity shows the catalytic activity of the reverse reaction of CoA-acylating aldehyde dehydrogenase)

Examples of genes include Q716S8 (*Clostridium beijerinckii*); Q7X4B7 (*Clostridium saccharoperbutylacetonicum*); A5HYN9 (*Clostridium botulinum*); P0A9Q7 (*E. coli*) (these are indicated by UniProtKB/Swiss-Prot No.); GenBank CAQ57983 (*Clostridium saccharobutylicum*); NCBI ZP_03705305 (*Clostridium methylpentosum*); NCBI_ZP 08533507 (*Caldalkalibacillus thermarum*) etc.

(h) Alcohol dehydrogenase (e.g., EC 1.1.1.1, EC 1.1.1.2 etc.)

Examples of genes include (each indicated by UniProtKB/Swiss-Prot No.) P0A4X1 (*Mycobacterium bovis*); P00331 (*Saccharomycess cerevisiae*); P00330 (*Saccharomycess cerevisiae*); Q9HIM3 (*Thermoplasma acidophilum*); B9WPR7 (*Arthrobacter* sp.); P00334 (*Drosophila melanogaster*) etc.

The enzymatic reaction step of the two stages of (g) and (h) can be catalyzed also by the action of aldehyde/alcohol dehydrogenase (adhE: EC1.1.1.1, 1.1.1.10 etc.). That is, adhE corresponds to both the above (g) and (h). Examples of adhE include D8GU53 (*Clostridium ljungdahlii*), D8GU52 (*Clostridium ljungdahlii*), Q9ANR5 (*Clostridium acetobutylicum*), P0A9Q7 (*E. coli*), and F7TVB7 (*Brevibacillus laterosporus*) (each indicated by UniProtKB/Swiss-Prot No.)

(i) 4-hydroxybutyraldehyde dehydrogenase

This enzyme is able to catalyze conversion from 4-hydroxybutyrate to 4-hydroxybutyraldehyde reversibly, and belongs to aldehyde dehydrogenase according to the enzymatic classification (e.g., EC 1.2.1.3, EC 1.2.1.4, EC 1.2.1.5 etc.)

Examples of genes of aldehyde dehydrogenase showing 4-hydroxybutyraldehyde dehydrogenase activity include (each indicated by UniProtKB/Swiss-Prot No.) E4R8S4 (*Pseudomonas putida*); P23883 (*E. coli*); P12693 (*Pseudomonas putida*); P40047 (*Saccharomyces cerevisiae*); P25553 (*E. coli*); POC6D7 (*Vibrio* sp.); P47771 (*Saccharomyces cerevisiae*); G3XYI2 (*Aspergillus niger*) etc.

(d) 2-oxoglutarate decarboxylase (e.g., EC 4.1.1.71)

Examples of genes include (each indicated by UniProtKB/Swiss-Prot No.) A0R2B1 (*Mycobacterium smegmatics*); I0WZ48 (*Rhodococcus imtechensis*); G2EJR8 (*Corynebacterium glutamicum*); J1S9U2 (*Streptomyces auratus*); J7LQH4 (*Arthrobacter* sp.) etc.

The kind (number) of genes of "1,4-butanediol biosynthesis related enzymes" to be introduced may be at least one as far as the recombinant cell is "capable of producing 1,4-butanediol from at least one C1 compound selected from the group consisting of methane, methanol, methylamine, formic acid, formaldehyde, and formamide". However, when the activity of each enzyme is enhanced by introducing two or more kinds of genes, improvement in productivity of 1,4-butanediol is expected. Basically, regarding a 1,4-butanediol biosynthesis related enzyme not possessed by the host cell, a gene encoding the enzyme is introduced externally. When the enzyme is possessed by the host cell, but its molecular activity is low, it is preferred to introduce a gene encoding an enzyme having higher molecular activity or the like.

The 1,4-butanediol biosynthesis related enzymes may be naturally occurring enzymes or enzymes modified therefrom. For example, amino acid substitution variants of each enzyme, and polypeptides that are partial fragments of each enzyme and have equivalent enzyme activity are also applicable.

In the recombinant cell of the present invention, other gene may further be introduced in addition to the gene encoding 1,4-butanediol biosynthesis related enzyme or the like. As a gene that is introduced, for example, the aforementioned methanol dehydrogenase gene, alcohol dehydrogenase gene, methane monooxydase gene, HPS/PHI gene, serine hydroxymethyltransferase gene, 5,10-methylene-tetrahydrofolic acid synthase gene, and serine hydroxymethyltransferase gene can be recited.

The method of introducing a gene into the host cell is not particularly limited, and may be selected appropriately depending on the kind of the host cell and the like. For example, a vector that can be introduced into the host cell and can allow expression of the gene incorporated therein may be used.

For example, when the host cell is a prokaryote such as a bacterium, a vector that can self duplicate or can be incorporated in chromosome in the host cell, and contains a promoter at the position allowing transcription of the inserted gene can be used. For example, it is preferred to construct in the host cell a series of structures including a promoter, a ribosome binding sequence, the above gene and a transcription termination sequence by using the vector.

For example, as a method of incorporating into chromosome of a methylotroph bacterium, exemplified is a method of destroying a target gene in *Methylobacillus flagellatus* having a ribulose monophosphate pathway, and in *Methylobacterium extorquencs* having a serine pathway (Chistoserdova L. et al., Microbiology 2000, 146, 233-238; Chistoserdov A Y., et al., J. Bacteriol 1994, 176, 4052-4065). While these are the methods for introducing a gene into a genome using cyclic DNA, a method for introducing a gene into genome using a linear DNA is also developed in *Methylophilus* bacteria and the like (see JP 2004-229662 A). In general, genomic recombination is more efficient by linear DNA than by cyclic DNA when the DNA is less susceptible to degradation by the host cell. Generally, in a homologous recombination method, it is preferred to target a gene existing in multi copies on the genome likewise an inverted-repeat sequence. As a technique for introducing multi copies into a genome, a method of carrying on a transposon is also known besides the homologous recombination. As a method of introducing a gene into a methylotrophic bacterium by a plasmid, for example, pAYC32 (Chistoserdov A Y., et al., Plasmid 1986, 16, 161-167), pRP301 (Lane M., et al., Arch. Microbiol. 1986, 144(1), 29-34), pBBR1, pBHR1 (Antoine R. et al., Molecular Microbiology 1992, 6, 1785-1799), and pCM80 (Marx C J. et al., Microbiology 2001, 147, 2065-2075) which are broad host range vectors are known.

A method of introducing a gene in methylotrophic yeast is established mainly in *Pichia pastoris*, and vectors such as pPIC3.5K, pPIC6, pGAPZ, and pFLD (available from Invitrogen) are commercially available.

As a plasmid that can be used for gene introduction into *Bacillus* bacteria, pMTLBS72 (Nguyen H D. Et al., Plasmid 2005, 54 (3), 241-248), pHT01 (available from Funakoshi Co., Ltd.), pHT43 (available from Funakoshi Co., Ltd.) and so on are available for *Bacillus subtilis*, p3STOP1623 hp (available from Funakoshi Co., Ltd.), pSP$_{YocH}$hp (available from Funakoshi Co., Ltd.) and so on are available for *Bacillus megaterium*, and pNI DNA (available from TAKARA BIO INC.) and so on are available for *Bacillus brevis*.

In introducing plural kinds of genes by using a vector, the genes may be incorporated into one vector, or incorporated into different vectors. Further, in incorporating a plurality of genes into one vector, the genes may be expressed under a common promotor, or may be expressed under different promotors. As an example of introducing plural kinds of genes, an embodiment of introducing the HPS/PHI gene in addition to "gene encoding 1,4-butanediol biosynthesis related enzymes" when the host cell is a methylotroph is recited.

As described above, while the known vectors that can be used in methylotroph and so on have been shown, the region involved in transcription control and replication regions such as promotor and terminator can be modified depending on the purpose. The modification includes change to other natural gene sequence in each host cell or its related species, and change to an artificial gene sequence.

By increasing the expression amount of the introduced gene in the host cell, the 1,4-butanediol discharging function and the 1,4-butanediol tolerance of the host cell by combining a variation technique such as mutation or genome shuffling in addition to the modification by the gene introduction as described above, it is possible to further improve the productivity of 1,4-butanediol.

That is, in the present invention, the foreign gene may be incorporated into a genome of the host cell, or incorporated into a plasmid.

In one preferred embodiment, the recombinant cell is tolerant to at least 400 mM 1,4-butanediol. In another preferred embodiment, the recombinant cell is tolerant to at least 2% (v/v) methanol. With such a configuration, it is possible to mass-produce 1,4-butanediol. For example, the recombinant cell having such characteristics can be obtained by subjecting host cells to an appropriate variation treatment to select a host cell having the intended characteristics, and using the host cell.

The present invention includes the following items (i) to (iv).

(i) A recombinant cell prepared by introducing a gene encoding at least one enzyme selected from the group consisting of succinate semialdehyde dehydrogenase, succinyl-CoA synthase, CoA-dependent succinate semialdehyde dehydrogenase, 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase into a host cell which is a methylotroph, a host cell into which a gene imparting a function of converting methanol and/or formic acid into formaldehyde, and a gene imparting formaldehyde fixing ability are introduced, or a host cell having a ribulose monophosphate pathway and into which a gene imparting a function of converting methanol and/or formic acid into formaldehyde is introduced, wherein the gene is expressed in the host cell, and the recombinant cell is capable of producing 1,4-butanediol from at least one C1 compound selected from the group consisting of methane, methanol, methylamine, formic acid, formaldehyde, and formamide.

(ii) A recombinant cell prepared by introducing a gene encoding at least one enzyme selected from the group consisting of succinate semialdehyde dehydrogenase, succinyl-CoA synthase, CoA-dependent succinate semialdehyde dehydrogenase, 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase into a host cell which is a methylotroph, wherein the gene is expressed in the host cell, and the recombinant cell is capable of producing 1,4-butanediol from at least one C1 compound selected from the group consisting of methane, methanol, methylamine, formic acid, formaldehyde, and formamide.

(iii) A recombinant cell prepared by introducing a gene imparting a function of converting methanol and/or formic acid into formaldehyde, a gene imparting formaldehyde fixing ability, and a gene encoding at least one enzyme selected from the group consisting of succinate semialdehyde dehydrogenase, succinyl-CoA synthase, CoA-dependent succinate semialdehyde dehydrogenase, 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase into a host cell, wherein the genes are expressed in the host cell, and the recombinant cell is capable of producing 1,4-butanediol from at least one C1 compound selected from the group consisting of methane, methanol, methylamine, formic acid, formaldehyde, and formamide.

(iv) A recombinant cell prepared by introducing a gene imparting a function of converting methanol and/or formic acid into formaldehyde, and a gene encoding at least one enzyme selected from the group consisting of succinate semialdehyde dehydrogenase, succinyl-CoA synthase, CoA-dependent succinate semialdehyde dehydrogenase, 2-oxoglutarate decarboxylase, 4-hydroxybutyrate dehydrogenase, 4-hydroxybutyryl-CoA transferase, 4-hydroxybutyryl-CoA reductase, 4-hydroxybutyraldehyde dehydrogenase, and alcohol dehydrogenase into a host cell having a ribulose monophosphate pathway, wherein the genes are expressed in the host cell, and the recombinant cell is capable of producing 1,4-butanediol from at least one C1 compound selected from the group consisting of methane, methanol, methylamine, formic acid, formaldehyde, and formamide.

In one aspect of the method for producing 1,4-butanediol of the present invention, the recombinant cell is cultured by using at least one C1 compound selected from the group consisting of methane, methanol, methylamine, formic acid, formaldehyde, and formamide as a carbon source, and the recombinant cell is caused to produce 1,4-butanediol. Regarding these C1 compounds used as a carbon source, one compound or a combination of two or more compounds may be used. These C1 compounds are preferably used as a main carbon source, and more preferably as a sole carbon source.

In the case of obligate methylotrophs, basically a synthetic culture medium containing a C1 compound as a sole carbon source is used, and addition of small amounts of natural culture medium such as yeast extract, corn steep liquor, and meat extract and vitamins to this culture medium promotes proliferation of bacteria. In the case of facultative methylotrophs, carbohydrates, lipids and the like, substances other than C1 compounds may be used as a carbon source in the bacterial proliferation stage, and in this case, the carbon source can be changed to the above C1 compound in the 1,4-butanediol production stage. Microorganisms can be cultured in any of aerobic, microaerobic, or anaerobic condition depending on the purpose. Any of the batch culture, feeding culture, and continuous culture can be employed.

For example, when methanol is used as a carbon source, it is typically used at a concentration of 1.0% (v/v) in the case of bacteria, or a concentration of 3.0% (v/v) or less in the case of yeasts, however, when the resistance to these is artificially modified, the culture can be also conducted with methanol of higher concentrations.

In another aspect of the method for producing 1,4-butanediol of the present invention, at least one C1 compound selected from the group consisting of methane, methanol, methylamine, formic acid, formaldehyde, and formamide are brought into contact with the recombinant cell, and the recombinant cell allows to produce 1,4-butanediol from the C1 compound. That is, regardless of whether cell division (cell proliferation) is involved or not, it is possible to produce 1,4-butanediol by bringing the C1 compound into contact with the recombinant cell. For example, it is possible to continuously produce 1,4-butanediol by continuously supplying a fixed recombinant cell with the C1 compound.

Also in the present aspect, regarding these C1 compounds, only one C1 compound may be used, or a combination of two or more C1 compounds may be used.

The produced 1,4-butanediol is accumulated in the cell or released outside the cell. For example, by collecting, isolating and purifying the 1,4-butanediol released outside the cell, it is possible to acquire purified 1,4-butanediol.

In the following, the present invention will be described more specifically by way of examples. However, the present invention is not limited to these examples.

EXAMPLE 1

Introduction of 1,4-butanediol (1,4-BDO) synthase gene into a methylotroph having the XuMP pathway, and production of 1,4-BDO from methanol using a recombinant In the present example, methanol assimilating yeast *Pichia pastolis* GS115 strain (available from Invitrogen) was used as a methylotroph having a XuMP pathway.

An artificial synthetic gene (7773 bp) of SEQ ID NO: 1 which is a 1,4-BDO biosynthesis related enzyme gene cluster was constructed. The gene cluster includes genes of sucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2).

An artificial synthetic gene of SEQ ID NO: 1 was cloned into SmaI/NotI cleavage site of pT7 blue-2 vector (available from Novagen). After mass-preparing the plasmid, the plasmid was cut with SmaI and NotI to obtain the inserted gene. The obtained gene fragment was introduced into SnaBI/NotI cleavage site of pPIC3.5K (available from Invitrogen) to construct a vector pPBDO in which 1,4-BDO synthetic gene is introduced. This vector allows expression of genes of sucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2) under the control by alcohol oxydase I (AOXI) promotor and AOXI terminator. By introducing this vector, it becomes possible to synthesize 1,4-BDO from succinyl CoA in yeasts.

Introduction of 1,4-BDO biosynthesis related enzyme gene expression unit by means of pPBDO into *Pichia pastoris* GS115 strain was conducted according to the Invitrogen Manual "Version D 032002/25-0156". For obtaining a multi-copy transformant, a strain tolerant to 1.5 mg/mL Geneticin (available from Invitrogen) was acquired. In this manner, methanol assimilating yeast GS115BDO strain having a plurality of copies of foreign 1,4-BDO biosynthesis related enzyme gene was constructed. As a control strain, GS11535K strain in which only pPIC3.5K is introduced, tolerant to 1.5 mg/mL Geneticin was obtained.

Each of GS115BDO strain and GS11535K strain was cultured aerobically at 30° C. for 64 hours in 20 mL of synthetic A culture containing methanol as a sole carbon source (containing 18 g of $H_3PO_4$, 14.28 g of $K_2SO_4$, 3.9 g of KOH, 0.9 g of $CaSO_4.2H_2O$, 11.7 g of $MgSO_4.7H_2O$, 8.4 mg of $CuSO_4.5H_2O$, 1.1 mg of KI, 4.2 mg of $MnSO_4H_2O$, 0.3 mg of $NaMoO_4.2H_2O$, 0.03 mg of $H_3BO_3$, 0.7 mg of $CoCl_2.6H_2O$, 28 mg of $ZnSO_4.7H_2O$, 91 mg of $FeSO_4.7H_2O$, 0.28 mg of biotin, 20 mL of methanol per 1 L). After collecting the cells, the collected cells were further cultured in 45 mL of synthetic A culture medium at 30° C. for another 16 hours under shaking. After end of the culture, the culture was centrifuged to obtain a culture supernatant. The culture supernatant was analyzed by LC/MS.

As a result, 1,4-BDO was not detected in GS11535K strain, but 1,4-BDO was detected significantly in GS115BDO strain. The concentration of generated 1,4-BDO was 13 mM.

These revealed that the present example allowed production of 1,4-BDO by eukaryotic microorganism (yeast) via a XuMP pathway which is one of methanol assimilating pathways.

EXAMPLE 2

Introduction of methanol dehydrogenase, HPS gene, PSI gene, and isoprene synthase gene into a non-methylotroph, and production of 1,4-BDO from methanol by a recombinant In the present example, *Bacillus subtilis* was used as a non-methylotroph.

An artificial synthetic gene (10600 bp) of SEQ ID NO: 6 which is a 1,4-BDO biosynthesis related enzyme gene cluster was constructed. The gene cluster includes genes of mdh (SEQ ID NO: 7: methanol dehydrogenase), HPS (SEQ ID NO: 8: 3-hexulose-6 phosphate synthase), PHI (SEQ ID NO: 9: 3-hexulose-6-phosphate isomerase), SucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2).

The artificial synthetic gene of SEQ ID NO: 6 was cloned into SmaI/XbaI cleavage site of pUC119. After mass-preparing the plasmid, the plasmid was cut with SmaI and XbaI to obtain the inserted gene. The obtained gene was introduced into XbaI/SmaI cleavage site of expression vector pHT01 (available from MoBiTec) for *Bacillus subtilis* to prepare pHTBDO. The vector pHTBDO allows expression of genes of mdh (SEQ ID NO: 7: methanol dehydrogenase), HPS (SEQ ID NO: 8: 3-hexulose-6 phosphate synthase), PHI (SEQ ID NO: 9: 3-hexulose-6-phosphate isomerase), SucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2).

As a control vector, an expression vector pHTMDH(-) in which MDH is removed from the group of seven enzymes encoded by pHTBDO was constructed. Further, an expression vector pHTBDO(-) in which SucD, 4HBd, abfT, and adhE2 which are 1,4-BDO biosynthesis related enzyme genes are removed from the group of seven enzymes encoded by pHTBDO was prepared.

According to the manual of MoBiTec "*Bacillus subtilis* Expression Vectors", each expression vector was introduced into *Bacillus subtilis* and a recombinant (recombinant cell) was prepared. In this manner, BSBDO strain having the expression vector pHTBDO, BSMDH(-) strain having the expression vector pHTMDH(-), and BSBDO(-) strain having the expression vector pHTBDO(-) were prepared, respectively.

Each recombinant was aerobically cultured at 37° C. in 100 mL of a methanol assimilating inductive culture medium (containing 10 mL of methanol, 3 g of ammonium phosphate, 1 g of potassium chloride, 0.1 g of magnesium sulfate heptahydrate, 0.5 g of yeast extract, 0.01 mM IPTG, and 5 mg of chloramphenicol in 1 L of tap water) until OD600 reached 1.5. After end of the culture, the culture supernatant was obtained by centrifugal separation and analyzed by LC/MS.

In BSBDO strain, 1,4-BDO was significantly detected, and the concentration was 9 mM (6 mM per 1OD600). On the other hand, in BSBDO(-) strain, 1,4-BDO was not detected. BSMDH(-) strain not having MDH little grew.

These revealed that by introducing MDH gene, HPS gene, and PHI gene to *Bacillus subtilis* which is a non-methylotroph, efficient growth in a culture medium containing methanol as a main carbon source was enabled, and by introducing 1,4-BDO biosynthesis related enzyme gene cluster (SEQ ID NO: 6), 1,4-BDO was generated efficiently.

EXAMPLE 3

Preparation of a methylotroph having a serine pathway into which 1,4-BDO biosynthesis related enzyme genes are introduced, and 1,4-BDO production from methanol by a recombinant In the present example, *Methylobacterium extorquens* (ATCC 55366) was used as a methylotroph having a serine pathway.

An artificial synthetic gene (6922 bp) of SEQ ID NO: 10 which is a 1,4-BDO biosynthesis related enzyme gene cluster was constructed. The gene cluster includes genes of SucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2).

The artificial synthetic gene of SEQ ID NO: 10 was cloned into HindIII/XbaI cleavage site of pUC119. After mass-preparing the plasmid, the plasmid was cut with HindIII and XbaI to obtain the inserted gene. The obtained gene was introduced into HindIII/XbaI site of broad host range vector pCM80 (Marx C J. et al., Microbiology 2001, 147, 2065-2075) to prepare pC80BDO. This vector allows expression of genes of SucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2). As codon modification of each enzyme gene, UUA (Leu) was transformed into UUG (Leu), and AUA (Ile) was transformed into AUC (Ile). The expression vector pC80BDO was introduced into *M. extorquens* by electroporation to obtain ME-BDO strain. As a control, an expression vector pCM80 was introduced into *M. extorquens* by electroporation to obtain ME-CM80 strain.

ME-BDO strain or ME-CM80 strain was aerobically cultured at 30° C. in 100 mL of a synthetic B culture medium containing methanol as a sole carbon source (containing 18 g of $H_3PO_4$, 14.28 g of $K_2SO_4$, 3.9 g of KOH, 0.9 g of $CaSO_4.2H_2O$, 11.7 g of $MgSO_4.7H_2O$, 8.4 mg of $CuSO_4.5H_2O$, 1.1 mg of KI, 4.2 mg of $MnSO_4H_2O$, 0.3 mg of $NaMoO_4.2H_2O$, 0.03 mg of $H_3BO_3$, 0.7 mg of $CoCl_2.6H_2O$, 28 mg of $ZnSO_4.7H_2O$, 91 mg of $FeSO_4.7H_2O$, 0.28 mg of biotin, 5 mL of methanol, and 10 mg of tetracycline per 1 L). The culture was continued until OD600 reached 1.8, and the culture supernatant was collected by centrifugal separation. The collected culture supernatant was analyzed by LC/MS.

In ME-BDO strain, 1,4-BDO was detected, and the concentration was 11 mM (6.2 mM per 1OD600). On the other hand, in ME-CM80 strain, 1,4-BDO was not detected.

These revealed that by introducing 1,4-BDO biosynthesis related enzyme gene cluster (SEQ ID NO: 10) into a methylotroph having a serine pathway, it was possible to efficiently produce 1,4-BDO from methanol.

EXAMPLE 4

Introduction of 1,4-BDO biosynthesis related enzyme gene into methylotroph having a RuMP pathway and 1,4-BDO production from methanol using a recombinant In the present example, *Methylophilus methylotrophus* (ATCC 53528) was used as a methylotroph having a RuMP pathway.

The pC80BDO prepared in Example 3 was introduced into *M. methylotrophus* by electroporation to obtain MM-BDO strain. As a control, pCM80 was introduced into *M. methylotrophus* by electroporation to obtain MM-CM80 strain.

MM-BDO strain or MM-CM80 strain was aerobically cultured at 37° C. in 100 mL of synthetic B culture medium containing methanol as a sole carbon source used in Example 3 (provided that the methanol concentration was set at 1% (v/v)). The culture supernatant was collected by centrifugal separation at the point of time when OD600 of the culture liquid was 1.8 to 2.0. The culture supernatant was analyzed by LC/MS. In MM-BDO strain, 1,4-BDO was detected, but in MM-80 strain, it was not detected. The accumulated concentration of 1,4-BDO produced by MM-BDO strain was 15 mM (8.3 mM per 1OD 600).

These revealed that by introducing 1,4-BDO biosynthesis related enzyme gene cluster (SEQ ID NO: 10) into a methylotroph having a RuMP pathway, it was possible to efficiently produce 1,4-BDO from methanol.

EXAMPLE 5

Introduction of methanol dehydrogenase (MDH) gene, HPS gene, PHI gene, and 1,4-BDO biosynthesis related enzyme gene into *Escherichia coli*, and production of 1,4-BDO from methanol by a recombinant An artificial synthetic gene (9123 bp) of SEQ ID NO: 11 which is a 1,4-BDO biosynthesis related enzyme gene cluster was constructed. The gene cluster includes genes of mdh (SEQ ID NO: 7: methanol dehydrogenase), HPS (SEQ ID NO: 8: 3-hexulose-6 phosphate synthase), PHI (SEQ ID NO: 9: 3-hexulose-6-phosphate isomerase), SucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2).

The artificial synthetic gene of SEQ ID NO: 11 was cloned into NcoI/HindIII cleavage site of a vector pTrc99A to prepare pTrcMeBDO. The pTrcMeBDO allows expression of genes of mdh (SEQ ID NO: 7: methanol dehydrogenase), HPS (SEQ ID NO: 8: 3-hexulose-6 phosphate synthase), PHI (SEQ ID NO: 9: 3-hexulose-6-phosphate isomerase), SucD (SEQ ID NO: 2: CoA-dependent succinate semialdehyde dehydrogenase), 4HBd (SEQ ID NO: 3: 4-hydroxybutyrate dehydrogenase), abfT (SEQ ID NO: 4: 4-hydroxybutyryl-CoA transferase), and adhE2 (SEQ ID NO: 5: aldehyde/alcohol dehydrogenase 2).

As a control vector, an expression vector pTrcMDH(-) in which MDH is removed from the group of seven enzymes encoded by pTrcMeBDO was constructed. Further, an expression vector pTrcBDO(-) in which SucD, 4HBd, abfT, and adhE2 which are 1,4-BDO biosynthesis related enzyme genes are removed from the group of seven enzymes encoded by pTrcMeBDO was prepared.

The expression vector pTrcMeBDO, pTrcMDH(-) or pTrcBDO(-) was introduced into *Escherichia coli* K12 strain, to obtain EKMeBDO strain, EKMDH(-) strain, and EKBDO(-) strain, respectively.

Each recombinant *Escherichia coli* was cultured aerobically at 37° C. in 100 mL of methanol assimilative synthetic C culture medium containing 0.05 mM IPTG (containing 18 g of $H_3PO_4$, 14.28 g of $K_2SO_4$, 3.9 g of KOH, 0.9 g of $CaSO_4.2H_2O$, 11.7 g of $MgSO_4.7H_2O$, 8.4 mg of $CuSO_4.5H_2O$, 1.1 mg of KI, 4.2 mg of $MnSO_4H_2O$, 0.3 mg of $NaMoO_4.2H_2O$, 0.03 mg of $H_3BO_3$, 0.7 mg of $CoCl_2.6H_2O$, 28 mg of $ZnSO_4.7H_2O$, 91 mg of $FeSO_4.7H_2O$, 0.28 mg of biotin, 5 mL of methanol, 34 mg of chloramphenicol, and 100 mg of ampicillin per 1 L). The culture supernatant was collected by centrifugal separation at the point of time when OD600 of the culture liquid was 1.0 to 1.6.

The collected culture supernatant was analyzed by LC/MS. 1,4-BDO was generated in an concentration of 11 mM (6.9 mM per 1OD600) in EKMeBDO strain, but 1,4-BDO was little detected in EKBDO(-) strain. EKMDH (-) strain perfectly failed to grow.

These revealed that by introducing MDH gene, HPS gene, and PHI gene into *Escherichia coli* which is a non-methylotroph, efficient growth in a culture medium containing methanol as a main carbon source was enabled, and by introducing 1,4-BDO biosynthesis related enzyme gene cluster (SEQ ID NO: 11), 1,4-BDO was generated efficiently.

The invention claimed is:

1. A recombinant cell prepared by introducing genes encoding a group of enzymes comprising CoA-dependent succinate semialdehyde dehydrogenase, 4-hydroxybutyrate dehydrogenase, 4-hydroxybutyryl-CoA transferase, 4-hydroxybutyryl-CoA reductase, and alcohol dehydrogenase, into a host cell which is a methylotroph, wherein the recombinant cell is non-naturally occurring, wherein the methylotroph belongs to genus *Methylobacterium* or genus *Methylophilus*, and wherein the genes are expressed in said recombinant cell, which is capable of producing 1,4-butanediol from methanol and is tolerant to at least 400 mM 1,4-butanediol and tolerant to at least 2% (v/v) methanol.

2. The recombinant cell according to claim 1, having at least one C1 carbon assimilating pathway selected from the group consisting of a serine pathway, a ribulose monophosphate pathway, and a xylulose monophosphate pathway as a fixing pathway of formaldehyde.

3. The recombinant cell according to claim 1, wherein a gene encoding 3-hexulose-6-phosphate synthase and a gene encoding 6-phospho-3-hexuloisomerase are further introduced, and the genes are expressed in the host cell.

4. A method for producing 1,4-butanediol, comprising culturing the recombinant cell according to claim 1 by using methanol as a carbon source, to cause the recombinant cell to produce 1,4-butanediol.

5. A method for producing 1,4-butanediol, comprising bringing methanol into contact with the recombinant cell according to claim 1, to cause the recombinant cell to produce 1,4-butanediol from the methanol.

* * * * *

SEQUENCE LISTING

<160> NUMBER OF SEQ ID NOS: 11

<210> SEQ ID NO 1
<211> LENGTH: 7773
<212> TYPE: DNA
<213> ORGANISM: Artificial
<220> FEATURE:
<223> OTHER INFORMATION: Synthetic gene cluster for 1,4-BDO synthesis in Pichia pastolis

<400> SEQUENCE: 1

| | | | | | |
|---|---|---|---|---|---|
| cccgggacca | tgggtaatga | agtatctata | aaagaattaa | ttgaaaaggc | aaaggtggca | 60 |
| caaaaaaat | tggaagccta | tagtcaagaa | caagttgatg | tactagtaaa | agcactagga | 120 |
| aaagtggttt | atgataatgc | agaaatgttt | gcaaaagaag | cagttgaaga | aacagaaatg | 180 |
| ggtgtttatg | aagataaagt | agctaaatgt | catttgaaat | caggagctat | ttggaatcat | 240 |
| ataaaagaca | agaaaactgt | aggcataata | aagaagaac | ctgaaagggc | acttgtttat | 300 |
| gttgctaagc | caagggagt | tgtggcagct | actacgccta | taactaatcc | agtggtaact | 360 |
| cctatgtgta | atgcaatggc | tgctataaag | ggcagaaata | caataatagt | agcaccacat | 420 |
| cctaaagcaa | agaaagtttc | agctcatact | gtagaactta | tgaatgctga | gcttaaaaaa | 480 |
| ttgggagcac | cagaaaatat | catacagata | gtagaagcac | catcaagaga | agctgctaag | 540 |
| gaacttatgg | aaagtgctga | tgtagttatt | gctacaggcg | gtgctggaag | agttaaagct | 600 |
| gcttactcca | gtggaagacc | agcttatggc | gttggacctg | aaattcaca | ggtaatagtt | 660 |
| gataagggat | acgattataa | caaagctgca | caggatataa | taacaggaag | aaaatatgac | 720 |
| aatggaatta | tatgttcttc | agagcaatca | gttatagctc | ctgctgaaga | ttatgataag | 780 |
| gtaatagcag | cttttgtaga | aaatgggca | ttctatgtag | aagatgagga | aacagtagaa | 840 |
| aagtttagat | caactttatt | taagatgga | aaaataaaca | gcaagattat | aggtaaatcc | 900 |
| gtccaaatta | ttgcggatct | tgcaggagta | aaagtaccag | aaggtactaa | ggttatagta | 960 |
| cttaagggta | aagtgcagg | agaaaaagat | gtactttgta | aagaaaaat | gtgtccagtt | 1020 |
| ttagtagcat | tgaaatatga | tacttttgaa | gaagcagttg | aaatagctat | ggctaattat | 1080 |
| atgtatgaag | gagctggtca | tacagcaggc | atacattctg | acaatgacga | gaacataaga | 1140 |
| tatgcaggaa | ctgtattacc | tataagcaga | ttagttgtaa | atcagcctgc | aactactgct | 1200 |
| ggaggaagtt | tcaataatgg | atttaaccct | actactacac | taggctgcgg | atcatggggc | 1260 |
| agaaacagta | tttcagaaaa | tcttacttac | gagcatctta | taaatgtttc | aagaataggg | 1320 |
| tatttcaata | aagaagcaaa | agttcctagc | tatgaggaaa | tatggggatg | atgattctta | 1380 |
| aataaacaat | acttaaaaca | tttgaggagg | tcttgtaaac | accatggaac | ttttcaaact | 1440 |
| caagagtgta | acacatcact | ttgacacttt | tgcagaattt | gccaaggaat | tctgtcttgg | 1500 |
| agaacgcgac | ttggtaatta | ccaacgagtt | catctatgaa | ccgtatatga | aggcatgcca | 1560 |
| gctccctgc | cattttgtta | tgcaggagaa | atatgggcaa | ggcgagcctt | ctgacgaaat | 1620 |
| gatgaataac | atcttggcag | acatccgtaa | tatccagttc | gaccgcgtaa | tcggtatcgg | 1680 |
| aggaggtacg | gttattgaca | tctctaaact | tttcgttctg | aaaggattaa | atgatgtact | 1740 |
| cgatgcattc | gaccgcaaaa | tacctcttat | caaagagaaa | gaactgatca | ttgtgcccac | 1800 |
| aacatgcgga | acgggtagcg | aggtgacgaa | catttctatc | gcagaaatca | aaagccgtca | 1860 |
| caccaaaatg | ggattggctg | acgatgccat | tgttgcagac | catgccatca | tcatacctga | 1920 |
| acttctgaag | agcttgcctt | tccacttcta | cgcatgcagt | gcaatcgatg | ctcttatcca | 1980 |

```
tgccatcgag tcatacgtat ctcctaaagc cagtccatat tctcgtctgt tcagtgaggc    2040
ggcttgggac attatcctgg aagtattcaa gaaaatcgcc gaacacggcc ctgaataccg    2100
cttcgaaaag ctgggagaaa tgatcatggc cagcaactat gccggtatag ccttcggaaa    2160
tgcaggagta ggagccgtcc acgcactatc ctacccgttg ggaggcaact atcacgtgcc    2220
gcatggagaa gcaaactatc agttcttcac agaggtattc aaagtatacc aaaagaagaa    2280
tcctttcggc tatatagtcg aactcaactg gaagctctcc aagatactga actgccagcc    2340
cgaatacgta tatccgaagc tggatgaact tctcggatgc cttcttacca agaaaccttt    2400
gcacgaatac ggcatgaagg acgaagaggt aagaggcttt gcggaatcag tgcttaagac    2460
acagcaaaga ttgctcgcca caactacgt agagcttact gtagatgaga tcgaaggtat     2520
ctacagaaga ctctactgat gaccttagac atgactgttc ctcagttcaa gttgggcact    2580
tacgagaaga ccggtcttgc tagattctaa tcaagaggat gtcagaatgc catttgcctg    2640 agatgcag gcttcatttt tgatactttt ttatttgtaa cctatatagt ataggatttt       2700
ttttgtcatt ttgtttcttc tcgtacgagc ttgctcctga tcagcctatc tcgcagctga    2760
tgaatatctt gtggtagggg tttgggaaaa tcattcgagt ttgatgtttt tcttggtatt    2820
tcccactcct cttcagagta cagaagatta agtgagaagt tcgtttgtgc aagcttagat    2880
ctaacatcca aagacgaaag gttgaatgaa acctttttgc catccgacat ccacaggtcc    2940
attctcacac ataagtgcca aacgcaacag gaggggatac actagcagca gaccgttgca    3000
aacgcaggac ctccactcct cttctcctca cacccacttt tgccatcga aaaaccagcc     3060 cagttattgg gcttgattgg agctcgctca ttccaattcc ttctattagg ctactaacac    3120 catgactta ttagcctgtc tatcctggcc cccctggcga ggttcatgtt tgtttatttc      3180
cgaatgcaac aagctccgca ttacacccga acatcactcc agatgagggc tttctgagtg    3240
tggggtcaaa tagtttcatg ttccccaaat ggcccaaaac tgacagttta aacgctgtct    3300
tggaacctaa tatgacaaaa gcgtgatctc atccaagatg aactaagttt ggttcgttga    3360
aatgctaacg gccagttggt caaaaagaaa cttccaaaag tcgccatacc gtttgtcttg    3420
tttggtattg attgacgaat gctcaaaaat aatctcatta atgcttagcg cagtctctct    3480
atcgcttctg aaccccggtg cacctgtgcc gaaacgcaaa tggggaaaca cccgcttttt    3540
ggatgattat gcattgtctc cacattgtat gcttccaaga ttctggtggg aatactgctg    3600
atagcctaac gttcatgatc aaaatttaac tgttctaacc cctacttgac agcaatatat    3660
aaacagaagg aagctgccct gtcttaaacc tttttttta tcatcattat tagcttactt      3720
tcataattgc gactggttcc aattgacaag cttttgattt taacgacttt taacgacaac    3780
ttgagaagat caaaaaacaa ctaattattc gaaccatgg aagttacaaa tcaaaaagaa     3840
ctaaaacaaa agctaaatga attgagagaa gcgcaaaaga agtttgcaac ctatactcaa    3900
gagcaagttg ataaaatttt taaacaatgt gccatagccg cagctaaaga aagaataaac    3960
ttagctaaat tagcagtaga agaaacagga ataggtcttg tagaagataa aatttataaaa   4020 aatcattttg cagcagaata tatatacaat aaatataaaa atgaaaaaac ttgtggcata    4080
atagaccatg acgattcttt aggcataaca aaggttgctg aaccaattgg aattgttgca    4140
gccatagttc ctactactaa tccaacttcc acagcaattt tcaaatcatt aatttcttta    4200
aaaacaagaa acgcaatatt cttttcacca catccacgtg caaaaaaatc tacaattgct    4260
gcagcaaaat taattttaga tgcagctgtt aaagcaggag cacctaaaaa tataataggc    4320
tggatagatg agccatcaat agaactttct caagatttga tgagtgaagc tgatataata    4380
```

```
ttagcaacag gaggtccttc aatggttaaa gcggcctatt catctggaaa acctgcaatt   4440
ggtgttggag caggaaatac accagcaata atagatgaga gtgcagatat agatatggca   4500
gtaagctcca taattttatc aaagacttat gacaatggag taatatgcgc ttctgaacaa   4560
tcaatattag ttatgaattc aatatacgaa aaagttaaag aggaatttgt aaaacgagga   4620
tcatatatac tcaatcaaaa tgaaatagct aaaataaaag aaactatgtt taaaaatgga   4680
gctattaatg ctgacatagt tggaaaatct gcttatataa ttgctaaaat ggcaggaatt   4740
gaagttcctc aaactacaaa gatacttata ggcgaagtac aatctgttga aaaaagcgag   4800
ctgttctcac atgaaaaact atcaccagta cttgcaatgt ataaagttaa ggattttgat   4860
gaagctctaa aaaaggcaca aaggctaata gaattaggtg aagtggaca cacgtcatct   4920 ttatatatag attcacaaaa caataaggat aaagttaaag aatttggatt agcaatgaaa   4980
acttcaagga catttattaa catgccttct tcacagggag caagcggaga tttatacaat   5040
tttgcgatag caccatcatt tactcttgga tgcggcactt ggggaggaaa ctctgtatcg   5100
caaaatgtag agcctaaaca tttattaaat attaaaagtg ttgctgaaag aagggaaaat   5160
atgctttggt ttaaagtgcc acaaaaaata tattttaaat atggatgtct tagatttgca   5220
ttaaaagaat taaagatat gaataagaaa agagccttta tagtaacaga taaagatctt   5280
tttaaacttg gatatgttaa taaaataaca aaggtactag atgagataga tattaaaatac   5340 agtatatttta cagatattaa atctgatcca actattgatt cagtaaaaaa aggtgctaaa   5400
gaaatgctta actttgaacc tgatactata atctctattg gtggtggatc gccaatggat   5460
gcagcaaagg ttatgcactt gttatatgaa tatccagaag cagaaattga aaatctagct   5520
ataaacttta tggatataag aaagagaata tgcaatttcc ctaaattagg tacaaaggcg   5580
atttcagtag ctattcctac aactgctggt accggttcag aggcaacacc ttttgcagtt   5640
ataactaatg atgaaacagg aatgaaatac cctttaactt cttatgaatt gaccccaaac   5700
atggcaataa tagatactga attaatgtta aatatgccta gaaaattaac agcagcaact   5760
ggaatagatg cattagttca tgctatagaa gcatatgttt cggttatggc tacggattat   5820
actgatgaat tagccttaag agcaataaaa atgatatttta aatatttgcc tagagcctat   5880
aaaaatggga ctaacgacat tgaagcaaga gaaaaaatgg cacatgcctc taatattgcg   5940
gggatggcat ttgcaaatgc tttcttaggt gtatgccatt caatggctca taacttgggg   6000
gcaatgcatc acgttccaca tggaattgct tgtgctgtat taatagaaga agttattaaa   6060
tataacgcta cagactgtcc aacaaagcaa acagcattcc ctcaatataa atctcctaat   6120
gctaagagaa aatatgctga aattgcagag tatttgaatt taaagggtac tagcgatacc   6180
gaaaaggtaa cagccttaat agaagctatt tcaaagttaa agatagattt gagtattcca   6240
caaaatataa gtgccgctgg aataaataaa aagatttttt ataatacgct agataaaatg   6300
tcagagcttg cttttgatga ccaatgtaca acagctaatc ctaggtatcc acttataagt   6360
gaacttaagg atatctatat aaaatcattt tgatgattct taaataaaca atacttaaaa   6420
catttgagga ggtcttgtaa acaccatgga ttggaagaag atctatgaag acagaacatg   6480
cactgcagat gaagcagtaa agagcattaa gtcaggtgac agagtgctat ttgcgcactg   6540
tgttgctgaa ccgccagttc ttgtagaagc aatggttgcg aatgcagctg catacaagaa   6600
tgtaacggtt tcacacatgg ttacccttgg aaagggtgaa tactcaaaac cagaatataa   6660
ggaaaacttt acttttgaag gttggtttac aagcccttca acaagaggat ccattgcaga   6720
```

```
aggacacgga cagtttgtcc ctgtattctt ccacgaggta ccatctttaa tcagaaaaga    6780
cattttccat gttgatgtat tcatggtaat ggtatcccct ccagatcata acggattctg    6840
ctgtgtgggt gtatcttctg actatacgat gcaggctatc aaatcagcaa aaattgtact    6900
tgctgaagta aatgatcagg tacctgtagt ttatggagat acatttgttc acgttagtga    6960
aatcgacaag ttcgtagaaa cttcacatcc acttccagaa atcggacttc ctaagatcgg    7020
tgaagtagaa gctgctattg gtaagcactg cgcttcccta atcgaagatg gttccacatt    7080
acagcttggt atcggagcta ttccggatgc tgtactttca cagcttaagg acaagaaaca    7140
ccttggtatc cactctgaaa tgatttccga cggtgttgta gatctttacg aagcaggcgt    7200
tatagactgc agccaaaagt ctatcgacaa aggcaaaatg gcaataacat tcttaatggg    7260
aacgaagaga ctttatgatt tcgctgcaaa caatccaaag gttgaattaa agccggttga    7320
ctacataaat catccatctg tagttgcaca gtgctccaaa atggtttgca tcaatgcttg    7380
cttgcaagtt gattttatgg gtcagattgt atccgatagt attgggacaa agcagttctc    7440
aggagtaggc ggtcaggttg acttcgtaag aggtgcatcc atgtctattg acggaaaagg    7500
taaagcgatc atcgcgatgc cttccgttgc aaagaagaag gatggaagta tgatttcgaa    7560
gatcgttcca ttcatcgatc acggtgcagc tgtaactaca tccagaaacg atgcggacta    7620
tgtcgtaacg gaatatggta ttgctgaaat gaagggtaag tctttacagg acagagcaag    7680
agcgttaatc aatattgcac accctgattt caaagatgaa ttaaaggctg aatttgaaaa    7740
gagattcaac gcggcattct gatgagcggc cgc                                 7773
```

<210> SEQ ID NO 2
<211> LENGTH: 1362
<212> TYPE: DNA
<213> ORGANISM: Clostridium kluyveri

<400> SEQUENCE: 2

```
atgagtaatg aagtatctat aaaagaatta attgaaaagg caaaggtggc acaaaaaaaa      60
ttggaagcct atagtcaaga acaagttgat gtactagtaa agcactagg aaaagtggtt     120 tatgataatg cagaaatgtt tgcaaaagaa gcagttgaag aaacagaaat gggtgtttat     180
gaagataaag tagctaaatg tcatttgaaa tcaggagcta tttggaatca tataaaagac     240
aagaaaactg taggcataat aaaagaagaa cctgaaaggg cacttgttta tgttgctaag     300
ccaaagggag ttgtggcagc tactacgcct ataactaatc cagtggtaac tcctatgtgt     360
aatgcaatgg ctgctataaa gggcagaaat acaataatag tagcaccaca tcctaaagca     420
aagaaagttt cagctcatac tgtagaactt atgaatgctg agcttaaaaa attgggagca     480
ccagaaaata tcatacagat agtagaagca ccatcaagag aagctgctaa ggaacttatg     540
gaaagtgctg atgtagttat tgctacaggc ggtgctggaa gagttaaagc tgcttactcc     600
agtggaagac cagcttatgg cgttggacct ggaaattcac aggtaatagt tgataaggga     660
tacgattata caaagctgc acaggatata ataacaggaa gaaaatatga caatggaatt     720
atatgttctt cagagcaatc agttatagct cctgctgaag attatgataa ggtaatagca     780
gcttttgtag aaatggggc attctatgta aagatgagg aaacagtaga aaagtttaga     840
tcaactttat ttaaagatgg aaaaataaac agcaagatta taggtaaatc cgtccaaatt     900
attgcggatc ttgcaggagt aaaagtacca gaaggtacta aggttatagt acttaagggt     960
aaaggtgcag gagaaaaaga tgtacttgt aaagaaaaaa tgtgtccagt tttagtagca     1020
ttgaaatatg atacttttga agaagcagtt gaaatagcta tggctaatta tatgtatgaa     1080
```

```
ggagctggtc atacagcagg catacattct gacaatgacg agaacataag atatgcagga   1140
actgtattac ctataagcag attagttgta aatcagcctg caactactgc tggaggaagt   1200
ttcaataatg gatttaaccc tactactaca ctaggctgcg gatcatgggg cagaaacagt   1260
atttcagaaa atcttactta cgagcatctt ataaatgttt caagaatagg gtatttcaat   1320
aaagaagcaa aagttcctag ctatgaggaa atatggggat aa                      1362
```

<210> SEQ ID NO 3
<211> LENGTH: 1116
<212> TYPE: DNA
<213> ORGANISM: Porphyromonas gingivalis

<400> SEQUENCE: 3

```
atgcaacttt tcaaactcaa gagtgtaaca catcactttg acacttttgc agaatttgcc     60
aaggaattct gtcttggaga acgcgacttg gtaattacca acgagttcat ctatgaaccg    120
tatatgaagg catgccagct cccctgccat tttgttatgc aggagaaata tgggcaaggc    180
gagccttctg acgaaatgat gaataacatc ttggcagaca tccgtaatat ccagttcgac    240
cgcgtaatcg gtatcggagg aggtacggtt attgacatct ctaaactttt cgttctgaaa    300
ggattaaatg atgtactcga tgcattcgac cgcaaaatac ctcttatcaa agagaaagaa    360
ctgatcattg tgcccacaac atgcggaacg ggtagcgagg tgacgaacat ttctatcgca    420
gaaatcaaaa gccgtcacac caaaatggga ttggctgacg atgccattgt tgcagaccat    480
gccatcatca tacctgaact tctgaagagc ttgcctttcc acttctacgc atgcagtgca    540
atcgatgctc ttatccatgc catcgagtca tacgtatctc ctaaagccag tccatattct    600
cgtctgttca gtgaggcggc ttgggacatt atcctggaag tattcaagaa aatcgccgaa    660
cacggccctg aataccgctt cgaaaagctg ggagaaatga tcatggccag caactatgcc    720
ggtatagcct tcggaaatgc aggagtagga gccgtccacg cactatccta cccgttggga    780
ggcaactatc acgtgccgca tggagaagca aactatcagt tcttcacaga ggtattcaaa    840
gtataccaaa agaagaatcc tttcggctat atagtcgaac tcaactggaa gctctccaag    900
atactgaact gccagcccga atacgtatat ccgaagctgg atgaacttct cggatgcctt    960
cttaccaaga aacctttgca cgaatacggc atgaaggacg aagaggtaag aggctttgcg   1020
gaatcagtgc ttaagacaca gcaaagattg ctcgccaaca actacgtaga gcttactgta   1080
gatgagatcg aaggtatcta cagaagactc tactaa                             1116
```

<210> SEQ ID NO 4
<211> LENGTH: 1317
<212> TYPE: DNA
<213> ORGANISM: Clostridium aminobutyricum

<400> SEQUENCE: 4

```
atggattgga agaagatcta tgaagacaga acatgcactg cagatgaagc agtaaagagc     60
attaagtcag gtgacagagt gctatttgcg cactgtgttg ctgaaccgcc agttcttgta    120
gaagcaatgg ttgcgaatgc agctgcatac aagaatgtaa cggtttcaca catggttacc    180
cttggaaagg gtgaatactc aaaaccagaa tataaggaaa actttacttt tgaaggttgg    240
tttacaagcc cttcaacaag aggatccatt gcagaaggac acggacagtt tgtccctgta    300
ttcttccacg aggtaccatc tttaatcaga aaagacattt tccatgttga tgtattcatg    360
gtaatggtat cccctccaga tcataacgga ttctgctgtg tgggtgtatc ttctgactat    420
```

```
acgatgcagg ctatcaaatc agcaaaaatt gtacttgctg aagtaaatga tcaggtacct      480
gtagtttatg gagatacatt tgttcacgtt agtgaaatcg acaagttcgt agaaacttca      540
catccacttc cagaaatcgg acttcctaag atcggtgaag tagaagctgc tattggtaag      600
cactgcgctt ccctaatcga agatggttcc acattacagc ttggtatcgg agctattccg      660
gatgctgtac tttcacagct taaggacaag aaacaccttg gtatccactc tgaaatgatt      720
tccgacggtg ttgtagatct ttacgaagca ggcgttatag actgcagcca aaagtctatc      780
gacaaaggca aaatggcaat aacattctta atgggaacga agagacttta tgatttcgct      840
gcaaacaatc caaggttga attaaagccg gttgactaca taaatcatcc atctgtagtt      900
gcacagtgct ccaaaatggt ttgcatcaat gcttgcttgc aagttgattt tatgggtcag      960
attgtatccg atagtattgg gacaaagcag ttctcaggag taggcggtca ggttgacttc     1020
gtaagaggtg catccatgtc tattgacgga aaaggtaaag cgatcatcgc gatgccttcc     1080
gttgcaaaga gaaggatgg aagtatgatt tcgaagatcg ttccattcat cgatcacggt     1140
gcagctgtaa ctacatccag aaacgatgcg gactatgtcg taacggaata tggtattgct     1200
gaaatgaagg gtaagtcttt acaggacaga gcaagagcgt taatcaatat tgcacaccct     1260
gatttcaaag atgaattaaa ggctgaattt gaaaagagat tcaacgcggc attctaa       1317

<210> SEQ ID NO 5
<211> LENGTH: 2577
<212> TYPE: DNA
<213> ORGANISM: Clostridium acetobutylicum

<400> SEQUENCE: 5
atgaaagtta caaatcaaaa agaactaaaa caaaagctaa atgaattgag agaagcgcaa       60
aagaagtttg caacctatac tcaagagcaa gttgataaaa ttttttaaaca atgtgccata      120 gccgcagcta agaaagaat aaacttagct aaattagcag tagaagaaac aggaataggt      180
cttgtagaag ataaaattat aaaaaatcat tttgcagcag aatatatata caataaatat      240
aaaaatgaaa aaacttgtgg cataatagac catgacgatt ctttaggcat aacaaaggtt      300
gctgaaccaa ttggaattgt tgcagccata gttcctacta ctaatccaac ttccacagca      360
attttcaaat cattaatttc tttaaaaaca agaaacgcaa tattctttc accacatcca      420 cgtgcaaaaa atctacaat tgctgcagca aaattaattt tagatgcagc tgttaaagca      480
ggagcaccta aaaatataat aggctggata gatgagccat caatagaact ttctcaagat      540
ttgatgagtg aagctgatat aatattagca acaggaggtc cttcaatggt taaagcggcc      600
tattcatctg gaaaacctgc aattggtgtt ggagcaggaa atacaccagc aataatagat      660
gagagtgcag atatagatat ggcagtaagc tccataattt tatcaaagac ttatgacaat      720
ggagtaatat gcgcttctga acaatcaata ttagttatga attcaatata cgaaaaagtt      780
aaagaggaat tgtaaaaacg aggatcatat atactcaatc aaaatgaaat agctaaaata      840
aaagaaacta tgtttaaaaa tggagctatt aatgctgaca tagttggaaa atctgcttat      900
ataattgcta aaatggcagg aattgaagtt cctcaaacta caaagatact tataggcgaa      960
gtacaatctt tgaaaaaag cgagctgttc tcacatgaaa aactatcacc agtacttgca     1020
atgtataaag ttaaggattt tgatgaagct ctaaaaaagg cacaaaggct aatagaatta     1080
ggtggaagtg gacacacgtc atctttatat atagattcac aaaacaataa ggataaagtt     1140
aaagaatttg gattagcaat gaaaacttca aggacatttt taacatgcc ttcttcacag     1200 ggagcaagcg gagatttata caattttgcg atagcaccat catttactct tggatgcggc     1260
```

```
acttggggag gaaactctgt atcgcaaaat gtagagccta acatttatt aaatattaaa        1320 agtgttgctg aaagaaggga aaatatgctt tggtttaaag tgccacaaaa aatatatttt        1380
aaatatggat gtcttagatt tgcattaaaa gaattaaaag atatgaataa gaaaagagcc        1440
tttatagtaa cagataaaga tcttttttaaa cttggatatg ttaataaaat aacaaaggta      1500
ctagatgaga tagatattaa atacagtata tttacagata ttaaatctga tccaactatt       1560
gattcagtaa aaaaaggtgc taaagaaatg cttaactttg aacctgatac tataatctct      1620
attggtggtg gatcgccaat ggatgcagca aaggttatgc acttgttata tgaatatcca      1680
gaagcagaaa ttgaaaatct agctataaac tttatggata taagaaagag aatatgcaat      1740
ttccctaaat taggtacaaa ggcgatttca gtagctattc ctacaactgc tggtaccggt      1800
tcagaggcaa cacctttttgc agttataact aatgatgaaa caggaatgaa atacccttta    1860
acttcttatg aattgaccccc aaacatggca ataatagata ctgaattaat gttaaatatg    1920
cctagaaaat aacagcagc aactggaata gatgcattag ttcatgctat agaagcatat      1980
gtttcggtta tggctacgga ttatactgat gaattagcct taagagcaat aaaaatgata    2040
tttaaatatt tgcctagagc ctataaaaat gggactaacg acattgaagc aagagaaaaa    2100
atggcacatg cctctaatat tgcggggatg gcatttgcaa atgctttctt aggtgtatgc    2160
cattcaatgg ctcataaact tggggcaatg catcacgttc cacatggaat tgcttgtgct    2220
gtattaatag aagaagttat taaatataac gctacagact gtccaacaaa gcaaacagca    2280
ttccctcaat ataaatctcc taatgctaag agaaaatatg ctgaaattgc agagtatttg    2340
aatttaaagg gtactagcga taccgaaaag gtaacagcct aatagaagc tatttcaaag    2400 ttaaagatag atttgagtat tccacaaaat ataagtgccg ctggaataaa taaaaaagat    2460
ttttataata cgctagataa aatgtcagag cttgcttttg atgaccaatg tacaacagct    2520
aatcctaggt atccacttat aagtgaactt aaggatatct atataaaatc attttaa     2577
```

<210> SEQ ID NO 6
<211> LENGTH: 10600
<212> TYPE: DNA
<213> ORGANISM: Artificial
<220> FEATURE:
<223> OTHER INFORMATION: Synthetic gene cluster for methanol-utilization and 1,4-BDO synthesis in Bacillus subtilis

<400> SEQUENCE: 6

```
tctagaatga caaactttttt cattccacca gccagcgtaa ttggacgagg tgcagtaaag      60
gaagtaggaa caagacttaa gcaaattgga gctaagaaag cgcttatcgt tacagatgca     120
tttcttcata gcacaggttt atctgaagaa gttgctaaaa acattcgtga agctggcctt     180
gatgttgcga ttttcccaaa agctcaacca gatccagcag atacacaagt tcatgaaggt     240
gtagatgtat tcaaacaaga aaactgtgat gcacttgttt ctatcggtgg aggtagctct    300
cacgatacag ctaaagcaat cggtttagtt gcagcaaacg gcggaagaat caatgactat    360
caaggtgtaa acagtgtaga aaaaccagtc gttccagtag ttgcaatcac tacaacagct    420
ggtactggta gtgaaacaac atctcttgca gttattacag actctgcacg taagtaaaa     480 atgcctgtta ttgatgagaa aattactcca actgtagcaa ttgttgaccc agaattaatg    540
gtgaaaaaac cagctggatt aacaatcgca actggtatgg acgcattatc acacgcaatt    600
gaagcatatg ttgcaaaagg tgctacacca gttactgatg catttgcaat tcaagcaatg    660
aaactcatca atgaatactt accaaaagcg gtggcaaacg gagaagacat cgaagcacgt    720
```

-continued

```
gaagcaatgg cttatgcaca atacatggca ggagtggcat ttaacaacgg tggtttagga      780
ttagtacact ctatttctca ccaagtaggt ggagtttaca aattacaaca cggaatctgt      840
aactcagtta atatgccaca cgtttgcgca ttcaacctaa ttgctaaaac tgagcgcttc      900
gcacacattg ctgagctttt aggcgagaat gtttctggct taagcactgc agcagctgct      960
gagagagcaa ttgtagcgct tgaacgctat aacaaaaact tcggtatccc atctggctat     1020
gcagaaatgg gcgtgaaaga agaggatatc gaattattag cgaaaaacgc attcgaagac     1080
gtatgtactc aaagcaaccc acgtgttgct acagttcaag acattgcaca aatcatcaaa     1140
aacgctctgt tgatgattct taaataaaca atacttaaaa catttgagga ggtcttgtaa     1200
acatggcatt gacacaaatg gcattagatt cactggattt cgacgcaact gttgcgctgg     1260
ctgaaaaggt agctccacac gttgacattc ttgaaatcgg tacaccatgc atcaagcaca     1320
acggtatcaa gttgctggaa actctgcgcg caaagttccc taacaacaag atcctggttg     1380
acctgaagac tatggatgct ggcttctacg aagctgagcc tttctacaag gctggtgctg     1440
atatcactac cgttctgggc gtagctgatc tgggtacaat caaaggcgta atcgacgctg     1500
ctaacaagta cggcaagaag gcacagatcg acctgatcaa tgttggtgat aaggctgctc     1560
gtactaagga agttgctaag ctgggcgcgc acatcattgg cgttcacact ggtctggacc     1620
aacaagctgc tggtcaaact ccttttgctg acctggcaac tgtaactggc ctgaacctgg     1680
gtctggaagt ttccgtagct ggtggtgtta agcctgctac tgttgcacaa gttaaagacg     1740
ctggtgctac catcatcgtc gctggcgctg ctatctacgg tgctgctgac ccagctgctg     1800
ctgctgctga atcactggc ctggctaagt gatgattctt aaataaacaa tacttaaaac     1860
atttgaggag gtcttgtaaa catgaacaaa tatcaagagc tcgtggtcag caagctgacc     1920
aatgttatca ataacactgc agaaggctat gacgacaaga ttttgagtct agtcgatgca     1980
gccggccgta catttatcgg tggtgctggc cgttccttgc tggtttcccg tttctttgca     2040
atgcgcttgg tgcatgcagg ttaccaagtt agcatggtcg gtgaagttgt tactccaagt     2100
atccaagctg gtgatctttt cattgtgatc tctggctctg gcagcacaga aaccctgatg     2160
cctttggtta agaaggcaaa gagccaaggt gccaagatta tcgtgatttc catgaaggct     2220
cagtccccaa tggctgaatt ggctgatctg gttgtgccag ttggtggcaa cgatgccaat     2280
gcatttgaca agactcatgg tatgcctatg gtactatttt cgagttgtc cacctgtgg     2340
ttcctcgaag cgactattgc caagctggta gatcaaaaag gtctgacaga agaaggtatg     2400
cgcgcgattc atgctaacct cgagtgatga tagcataacc ccttggggcc tctaaacggg     2460
tcttgagggg ttttttggag ctcaggcctt aactcacatt aattgcgttg cgctcactgc     2520
ccgctttcca gtcgggaaac ctgtcgtgcc agctgcatta atgaatcggc caacgcgcgg     2580
ggagaggcgg tttgcgtatt gggcgccagg gtggttttc ttttcaccag tgagacgggc     2640
aacagctgat tgcccttcac cgcctggccc tgagagagtt gcagcaagcg tccacgctg     2700
gtttgcccca gcaggcgaaa atcctgtttg atggtggtta acggcgggat ataacatgag     2760
ctgtcttcgg tatcgtcgta tcccactacc gagatatccg caccaacgcg cagcccggac     2820
tcggtaatgg cgcgcattgc gcccagcgcc atctgatcgt tggcaaccag catccgcagtg     2880
ggaacgatgc cctcattcag catttgcatg gtttgttgaa aaccggacat ggcactccag     2940
tcgccttccc gttccgctat cggctgaatt tgattgcgag tgagatattt atgccagcca     3000
gccagacgca gacgcgccga gacagaactt aatgggcccg ctaacagcgc gatttgctgg     3060
```

-continued

```
tgacccaatg cgaccagatg ctccacgccc agtcgcgtac cgtcttcatg ggagaaaata    3120
atactgttga tgggtgtctg gtcagagaca tcaagaaata cgccggaac attagtgcag     3180 gcagcttcca cagcaatggc atcctggtca tccagcggat agttaatgat cagcccactg    3240
acgcgttgcg cgagaagatt gtgcaccgcc gttttacagg cttcgacgcc gcttcgttct    3300
accatcgaca ccaccacgct ggcacccagt tgatcggcgc gagatttaat cgccgcgaca    3360
atttgcgacg gcgcgtgcag ggccagactg gaggtggcaa cgccaatcag caacgactgt    3420
ttgcccgcca gttgttgtgc cacgcggttg ggaatgtaat tcagctccgc catcgccgct    3480
tccacttttt cccgcgtttt cgcagaaacg tggctggcct ggttcaccac gcgggaaacg    3540
gtctgataag agacaccggc atactctgcg acatcgtata acgttactgg tttcatcaaa    3600
atcgtctccc tccgtttgaa tatttgattg atcgtaacca gatgaagcac tctttccact    3660
atccctacag tgttatggct tgaacaatca cgaaacaata attggtacgt acgatctttc    3720
agccgactca aacatcaaat cttacaaatg tagtctttga agtattaca tatgtaagat     3780 ttaaatgcaa ccgttttttc ggaaggaaat gatgacctcg tttccaccgg aattagcttg    3840
gtaccagcta ttgtaacata atcggtacgg gggtgaaaaa gctaacggaa aagggagcgg    3900
aaaagaatga tgtaagcgtg aaaaatttt tatcttatca cttgaaattg gaagggagat     3960
tctttattat aagaattgtg gaattgtgag cggataacaa ttcccaatta aggaggaag     4020 gatccatgag taatgaagta tctataaaag aattaattga aaaggcaaag gtggcacaaa    4080
aaaaattgga agcctatagt caagaacaag ttgatgtact agtaaaagca ctaggaaaag    4140
tggtttatga taatgcagaa atgtttgcaa agaagcagt tgaagaaaca gaaatgggtg      4200
tttatgaaga taaagtagct aaatgtcatt tgaaatcagg agctatttgg aatcatataa    4260
aagacaagaa aactgtaggc ataataaaag aagaacctga agggcactt gtttatgttg      4320 ctaagccaaa gggagttgtg gcagctacta cgcctataac taatccagtg gtaactccta    4380
tgtgtaatgc aatggctgct ataaagggca gaaatacaat aatagtagca ccacatccta    4440 agcaaagaa agtttcagct catactgtag aacttatgaa tgctgagctt aaaaaattgg     4500
gagcaccaga aaatatcata cagatagtag aagcaccatc aagagaagct gctaaggaac    4560
ttatggaaag tgctgatgta gttattgcta caggcggtgc tggaagagtt aaagctgctt    4620
actccagtgg aagaccagct tatggcgttg gacctggaaa ttcacaggta atagttgata    4680
agggatacga ttataacaaa gctgcacagg atataataac aggaagaaaa tatgacaatg    4740
gaattatatg ttcttcagag caatcagtta tagctcctgc tgaagattat gataaggtaa    4800
tagcagcttt tgtagaaaat ggggcattct atgtagaaga tgaggaaaca gtagaaaagt    4860
ttagatcaac tttatttaaa gatggaaaaa taaacagcaa gattataggt aaatccgtcc    4920
aaattattgc ggatcttgca ggagtaaaag taccagaagg tactaaggtt atagtactta    4980
agggtaaagg tgcaggagaa aaagatgtac tttgtaaaga aaaaatgtgt ccagttttag    5040
tagcattgaa atatgatact tttgaagaag cagttgaaat agctatggct aattatatgt    5100
atgaaggagc tggtcataca gcaggcatac attctgacaa tgacgagaac ataagatatg    5160
caggaactgt attacctata agcagattag ttgtaaatca gcctgcaact actgctggag    5220
gaagtttcaa taatggattt aaccctacta ctacactagg ctgcggatca tggggcagaa    5280
acagtatttc agaaaatctt acttacgagc atcttataaa tgtttcaaga atagggtatt    5340
tcaataaaga agcaaaagtt cctagctatg aggaaatatg gggatgatga ttcttaaata    5400
aacaatactt aaaacatttg aggaggtctt gtaaacatgc aactttttcaa actcaagagt    5460
```

```
gtaacacatc actttgacac ttttgcagaa tttgccaagg aattctgtct tggagaacgc    5520
gacttggtaa ttaccaacga gttcatctat gaaccgtata tgaaggcatg ccagctcccc    5580
tgccattttg ttatgcagga gaaatatggg caaggcgagc cttctgacga aatgatgaat    5640
aacatcttgg cagacatccg taatatccag ttcgaccgcg taatcggtat cggaggaggt    5700
acggttattg acatctctaa acttttcgtt ctgaaaggat taaatgatgt actcgatgca    5760
ttcgaccgca aaatacctct tatcaaagag aaagaactga tcattgtgcc cacaacatgc    5820
ggaacgggta gcgaggtgac gaacatttct atcgcagaaa tcaaaagccg tcacaccaaa    5880
atgggattgc tgacgatgc cattgttgca gaccatgcca tcatcatacc tgaacttctg    5940
aagagcttgc ctttccactt ctacgcatgc agtgcaatcg atgctcttat ccatgccatc    6000
gagtcatacg tatctcctaa agccagtcca tattctcgtc tgttcagtga ggcggcttgg    6060
gacattatcc tggaagtatt caagaaaatc gccgaacacg ccctgaata ccgcttcgaa     6120 aagctgggag aaatgatcat ggccagcaac tatgccggta tagccttcgg aaatgcagga    6180
gtaggagccg tccacgcact atcctacccg ttgggaggca actatcacgt gccgcatgga    6240
gaagcaaact atcagttctt cacagaggta ttcaaagtat accaaaagaa gaatcctttc    6300
ggctatatag tcgaactcaa ctggaagctc tccaagatac tgaactgcca gcccgaatac    6360
gtatatccga agctggatga acttctcgga tgccttctta ccaagaaacc tttgcacgaa    6420
tacggcatga aggacgaaga ggtaagaggc tttgcggaat cagtgcttaa gacacagcaa    6480
agattgctcg ccaacaacta cgtagagctt actgtagatg agatcgaagg tatctacaga    6540
agactctact gatgattctt aaataaacaa tacttaaaac atttgaggag gtcttgtaaa    6600
catggattgg aagaagatct atgaagacag aacatgcact gcagatgaag cagtaaagag    6660
cattaagtca ggtgacagag tgctatttgc gcactgtgtt gctgaaccgc cagttcttgt    6720
agaagcaatg gttgcgaatg cagctgcata caagaatgta acggtttcac acatggttac    6780
ccttggaaag ggtgaatact caaaaccaga atataaggaa aactttactt ttgaaggttg    6840
gtttacaagc ccttcaacaa gaggatccat tgcagaagga cacggacagt tgtccctgt     6900 attcttccac gaggtaccat cttaatcag aaaagacatt ttccatgttg atgtattcat      6960
ggtaatggta tccctccag atcataacgg attctgctgt gtgggtgtat cttctgacta     7020
tacgatgcag gctatcaaat cagcaaaaat tgtacttgct gaagtaaatg atcaggtacc    7080
tgtagtttat ggagatacat ttgttcacgt tagtgaaatc gacaagttcg tagaaacttc    7140
acatccactt ccagaaatcg gacttcctaa gatcggtgaa gtagaagctg ctattggtaa    7200
gcactgcgct tccctaatcg aagatggttc cacattacag cttggtatcg gagctattcc    7260
ggatgctgta ctttcacagc ttaaggacaa gaaaacacctt ggtatccact ctgaaatgat   7320
ttccgacggt gttgtagatc tttacgaagc aggcgttata gactgcagcc aaaagtctat    7380
cgacaaaggc aaaatggcaa taacattctt aatgggaacg aagagacttt atgatttcgc    7440
tgcaaacaat ccaaaggttg aattaaagcc ggttgactac ataaatcatc catctgtagt    7500
tgcacagtgc tccaaaatgg tttgcatcaa tgcttgcttg caagttgatt ttatgggtca    7560
gattgtatcc gatagtattg ggacaaagca gttctcagga gtaggcggtc aggttgactt    7620
cgtaagaggt gcatccatgt ctattgacgg aaaaggtaaa gcgatcatcg cgatgccttc    7680
cgttgcaaag aagaaggatg gaagtatgat ttcgaagatc gttccattca tcgatcacgg    7740
tgcagctgta actacatcca gaaacgatgc ggactatgtc gtaacggaat atggtattgc    7800
```

```
tgaaatgaag ggtaagtctt tacaggacag agcaagagcg ttaatcaata ttgcacaccc   7860
tgatttcaaa gatgaattaa aggctgaatt tgaaaagaga ttcaacgcgg cattctgatg   7920
attcttaaat aaacaatact taaaacattt gaggaggtct tgtaaacatg aaagttacaa   7980
atcaaaaaga actaaaacaa aagctaaatg aattgagaga agcgcaaaag aagttttgcaa  8040 cctatactca agagcaagtt gataaaattt ttaaacaatg tgccatagcc gcagctaaag   8100
aaagaataaa cttagctaaa ttagcagtag aagaaacagg aataggtctt gtagaagata   8160
aaattataaa aaatcatttt gcagcagaat atatatacaa taaatataaa aatgaaaaaa   8220
cttgtggcat aatagaccat gacgattctt taggcataac aaaggttgct gaaccaattg   8280
gaattgttgc agccatagtt cctactacta atccaacttc cacagcaatt ttcaaatcat   8340
taatttcttt aaaaacaaga aacgcaatat tcttttcacc acatccacgt gcaaaaaaat   8400
ctacaattgc tgcagcaaaa ttaattttag atgcagctgt taaagcagga gcacctaaaa   8460
atataatagg ctggatagat gagccatcaa tagaactttc tcaagatttg atgagtgaag   8520
ctgatataat attagcaaca ggaggtcctt caatggttaa agcggcctat tcatctggaa   8580
aacctgcaat tggtgttgga gcaggaaata caccagcaat aatagatgag agtgcagata   8640
tagatatggc agtaagctcc ataatttat caaagactta tgacaatgga gtaatatgcg    8700
cttctgaaca atcaatatta gttatgaatt caatatacga aaaagttaaa gaggaatttg   8760
taaaacgagg atcatatata ctcaatcaaa atgaaatagc taaaataaaa gaaactatgt   8820
ttaaaaatgg agctattaat gctgacatag ttggaaaatc tgcttatata attgctaaaa   8880
tggcaggaat tgaagttcct caaactacaa agatacttat aggcgaagta caatctgttg   8940
aaaaaagcga gctgttctca catgaaaaac tatcaccagt acttgcaatg tataaagtta   9000
aggattttga tgaagctcta aaaaaggcac aaaggctaat agaattaggt ggaagtggac   9060
acacgtcatc tttatatata gattcacaaa acaataagga taaagttaaa gaatttggat   9120
tagcaatgaa aacttcaagg acatttatta acatgccttc ttcacaggga gcaagcggag   9180
atttatacaa ttttgcgata gcaccatcat ttactcttgg atgcggcact tggggaggaa   9240
actctgtatc gcaaaatgta gagcctaaac atttattaaa tattaaaagt gttgctgaaa   9300
gaagggaaaa tatgctttgg tttaaagtgc cacaaaaaat atattttaaa tatggatgtc   9360
ttagatttgc attaaaagaa ttaaaagata tgaataagaa aagagccttt atagtaacag   9420
ataaagatct tttttaaactt ggatatgtta ataaaataac aaaggtacta gatgagatag   9480
atattaaata cagtatattt acagatatta aatctgatcc aactattgat tcagtaaaaa   9540
aaggtgctaa agaaatgctt aactttgaac ctgatactat aatctctatt ggtggtggat   9600
cgccaatgga tgcagcaaag gttatgcact tgttatatga atatccagaa gcagaaattg   9660
aaaatctagc tataaacttt atggatataa gaaagagaat atgcaatttc cctaaattag   9720
gtacaaaggc gatttcagta gctattccta caactgctgg taccggttca gaggcaacac   9780
cttttgcagt tataactaat gatgaaacag gaatgaaata cccttaact tcttatgaat   9840 tgacccaaaa catggcaata atagatactg aattaatgtt aaatatgcct agaaaattaa   9900
cagcagcaac tggaatagat gcattagttc atgctataga agcatatgtt tcggttatgg   9960
ctacggatta tactgatgaa ttagccttaa gagcaataaa aatgatattt aaatatttgc  10020
ctagagccta taaaaatggg actaacgaca ttgaagcaag agaaaaaatg gcacatgcct  10080
ctaatattgc ggggatggca tttgcaaatg cttttcttagg tgtatgccat tcaatggctc  10140
ataaacttgg ggcaatgcat cacgttccac atggaattgc ttgtgctgta ttaatagaag  10200
```

```
aagttattaa atataacgct acagactgtc caacaaagca aacagcattc cctcaatata    10260
aatctcctaa tgctaagaga aaatatgctg aaattgcaga gtatttgaat ttaaagggta    10320
ctagcgatac cgaaaaggta acagccttaa tagaagctat ttcaaagtta aagatagatt    10380
tgagtattcc acaaaatata agtgccgctg aataaaataa aaaagatttt tataatacgc    10440
tagataaaat gtcagagctt gcttttgatg accaatgtac aacagctaat cctaggtatc    10500
cacttataag tgaacttaag gatatctata taaaatcatt ttgatgatag cataacccct    10560
tggggcctct aaacgggtct tgaggggttt tttgcccggg                          10600
```

<210> SEQ ID NO 7
<211> LENGTH: 1146
<212> TYPE: DNA
<213> ORGANISM: Bacillus methanolicus

<400> SEQUENCE: 7

```
atgacaaact ttttcattcc accagccagc gtaattggac gaggtgcagt aaaggaagta      60
ggaacaagac ttaagcaaat tggagctaag aaagcgctta tcgttacaga tgcatttctt     120
catagcacag gttatctgaa agaagttgct aaaaacattc gtgaagctgg ccttgatgtt     180
gcgattttcc caaaagctca accagatcca gcagatacac aagttcatga aggtgtagat     240
gtattcaaac aagaaaactg tgatgcactt gtttctatcg gtggaggtag ctctcacgat     300
acagctaaag caatcggttt agttgcagca acggcggaa gaatcaatga ctatcaaggt     360
gtaaacagtg tagaaaaacc agtcgttcca gtagttgcaa tcactacaac agctggtact     420
ggtagtgaaa caacatctct tgcagttatt acagactctg cacgtaaagt aaaaatgcct     480
gttattgatg agaaaattac tccaactgta gcaattgttg acccagaatt aatggtgaaa     540
aaaccagctg gattaacaat cgcaactggt atggacgcat tatcacacgc aattgaagca     600
tatgttgcaa aaggtgctac accagttact gatgcatttg caattcaagc aatgaaactc     660
atcaatgaat acttaccaaa agcggtggca acggagaag catcgaagc acgtgaagca     720 atggcttatg cacaatacat ggcaggagtg gcatttaaca acggtggttt aggattagta     780
cactctattt ctcaccaagt aggtggagtt tacaaattac aacacggaat ctgtaactca     840
gttaatatgc cacacgtttg cgcattcaac ctaattgcta aaactgagcg cttcgcacac     900
attgctgagc ttttaggcga gaatgtttct ggcttaagca ctgcagcagc tgctgagaga     960
gcaattgtag cgcttgaacg ctataacaaa aacttcggta tcccatctgg ctatgcagaa    1020
atgggcgtga agaagagga tatcgaatta ttagcgaaaa acgcattcga agacgtatgt    1080
actcaaagca acccacgtgt tgctacagtt caagacattg cacaaatcat caaaaacgct    1140
ctgtaa                                                              1146
```

<210> SEQ ID NO 8
<211> LENGTH: 630
<212> TYPE: DNA
<213> ORGANISM: Methylomonas aminofaciens

<400> SEQUENCE: 8

```
atggcattga cacaaatggc attagattca ctgatttcg acgcaactgt tgcgctggct      60
gaaaaggtag ctccacacgt tgacattctt gaaatcggta caccatgcat caagcacaac    120
ggtatcaagt tgctggaaac tctgcgcgca aagttcccta acaacaagat cctggttgac    180
ctgaagacta tggatgctgg cttctacgaa gctgagcctt tctacaaggc tggtgctgat    240
```

| | |
|---|---|
| atcactaccg ttctgggcgt agctgatctg ggtacaatca aaggcgtaat cgacgctgct | 300 |
| aacaagtacg gcaagaaggc acagatcgac ctgatcaatg ttggtgataa ggctgctcgt | 360 |
| actaaggaag ttgctaagct gggcgcgcac atcattggcg ttcacactgg tctgaccaa | 420 |
| caagctgctg gtcaaactcc ttttgctgac ctggcaactg taactggcct gaacctgggt | 480 |
| ctggaagttt ccgtagctgg tggtgttaag cctgctactg ttgcacaagt taaagacgct | 540 |
| ggtgctacca tcatcgtcgc tggcgctgct atctacggtg ctgctgaccc agctgctgct | 600 |
| gctgctgaaa tcactggcct ggctaagtaa | 630 |

<210> SEQ ID NO 9
<211> LENGTH: 546
<212> TYPE: DNA
<213> ORGANISM: Methylomonas aminofaciens

<400> SEQUENCE: 9

| | |
|---|---|
| atgaacaaat tcaagagct cgtggtcagc aagctgacca atgttatcaa taacactgca | 60 |
| gaaggctatg acgacaagat tttgagtcta gtcgatgcag ccggccgtac atttatcggt | 120 |
| ggtgctggcc gttccttgct ggtttcccgt ttctttgcaa tgcgcttggt gcatgcaggt | 180 |
| taccaagtta gcatggtcgg tgaagttgtt actccaagta tccaagctgg tgatcttttc | 240 |
| attgtgatct ctggctctgg cagcacagaa accctgatgc ctttggttaa gaaggcaaag | 300 |
| agccaaggtg ccaagattat cgtgatttcc atgaaggctc agtccccaat ggctgaattg | 360 |
| gctgatctgg ttgtgccagt tggtggcaac gatgccaatg catttgacaa gactcatggt | 420 |
| atgcctatgg gtactatttt cgagttgtcc accctgtggt tcctcgaagc gactattgcc | 480 |
| aagctggtag atcaaaaagg tctgacagaa gaaggtatgc gcgcgattca tgctaacctc | 540 |
| gagtaa | 546 |

<210> SEQ ID NO 10
<211> LENGTH: 6922
<212> TYPE: DNA
<213> ORGANISM: Artificial
<220> FEATURE:
<223> OTHER INFORMATION: Synthetic gene cluster for 1,4-BDO synthesis in
      Methylobacterium extorquens

<400> SEQUENCE: 10

| | |
|---|---|
| aagcttatga gtaatgaagt atctatcaaa gaattgattg aaaaggcaaa ggtggcacaa | 60 |
| aaaaaattgg aagcctatag tcaagaacaa gttgatgtac tagtaaaagc actaggaaaa | 120 |
| gtggtttatg ataatgcaga aatgtttgca aagaagcag ttgaagaaac agaaatgggt | 180 |
| gtttatgaag ataaagtagc taaatgtcat ttgaaatcag gagctatttg gaatcatatc | 240 |
| aaagacaaga aaactgtagg catcatcaaa gaagaacctg aaagggcact tgtttatgtt | 300 |
| gctaagccaa agggagttgt ggcagctact acgcctatca ctaatccagt ggtaactcct | 360 |
| atgtgtaatg caatggctgc tatcaagggc agaaatacaa tcattgtagc accacatcct | 420 |
| aaagcaaaga agtttcagc tcatactgta gaacttatga atgctgagct taaaaaattg | 480 |
| ggagcaccag aaaatatcat ccagatcgta gaagcaccat caagagaagc tgctaaggaa | 540 |
| cttatggaaa gtgctgatgt agttattgct acaggcggtg ctggaagagt taaagctgct | 600 |
| tactccagtg gaagaccagc ttatggcgtt ggacctggaa attcacaggt aatcgttgat | 660 |
| aagggatacg attataacaa agctgcacag gatatcatca caggaagaaa atatgacaat | 720 |
| ggaattatct gttcttcaga gcaatcagtt atcgctcctg ctgaagatta tgataaggta | 780 |

```
atcgcagctt ttgtagaaaa tggggcattc tatgtagaag atgaggaaac agtagaaaag    840
tttagatcaa ctttgtttaa agatggaaaa atcaacagca agattatcgg taaatccgtc    900
caaattattg cggatcttgc aggagtaaaa gtaccagaag gtactaaggt tatcgtactt    960
aagggtaaag gtgcaggaga aaaagatgta ctttgtaaag aaaaaatgtg tccagttttg   1020
gtagcattga aatatgatac ttttgaagaa gcagttgaaa tcgctatggc taattatatg   1080
tatgaaggag ctggtcatac agcaggcatc cattctgaca atgacgagaa catcagatat   1140
gcaggaactg tattacctat cagcagattg gttgtaaatc agcctgcaac tactgctgga   1200
ggaagtttca ataatggatt taaccctact actacactag gctgcggatc atggggcaga   1260
aacagtattt cagaaaatct tacttacgag catcttatca atgtttcaag aatcgggtat   1320
ttcaataaag aagcaaaagt tcctagctat gaggaaatct ggggatgatg attcttaaat   1380
aaacaatact taaaacattt gaggaggtct tgtaaacatg caacttttca aactcaagag   1440
tgtaacacat cactttgaca cttttgcaga atttgccaag gaattctgtc ttggagaacg   1500
cgacttggta attaccaacg agttcatcta tgaaccgtat atgaaggcat gccagctccc   1560
ctgccatttt gttatgcagg agaaatatgg gcaaggcgag ccttctgacg aaatgatgaa   1620
taacatcttg gcagacatcc gtaatatcca gttcgaccgc gtaatcggta tcggaggagg   1680
tacggttatt gacatctcta aacttttcgt tctgaaagga ttaaatgatg tactcgatgc   1740
attcgaccgc aaaatccctc ttatcaaaga gaaagaactg atcattgtgc ccacaacatg   1800
cggaacgggt agcgaggtga cgaacatttc tatcgcagaa atcaaaagcc gtcacaccaa   1860
aatgggattg gctgacgatg ccattgttgc agaccatgcc atcatcatcc ctgaacttct   1920
gaagagcttg cctttccact tctacgcatg cagtgcaatc gatgctctta tccatgccat   1980
cgagtcatac gtatctccta aagccagtcc atattctcgt ctgttcagtg aggcggcttg   2040
ggacattatc ctggaagtat tcaagaaaat cgccgaacac ggccctgaat accgcttcga   2100
aaagctggga gaaatgatca tggccagcaa ctatgccggt atcgccttcg gaaatgcagg   2160
agtaggagcc gtccacgcac tatcctaccc gttgggaggc aactatcacg tgccgcatgg   2220
agaagcaaac tatcagttct tcacagaggt attcaaagta taccaaaaga gaatccttt   2280 cggctatatc gtcgaactca actggaagct ctccaagatc ctgaactgcc agcccgaata   2340
cgtatatccg aagctggatg aacttctcgg atgccttctt accaagaaac ctttgcacga   2400
atacggcatg aaggacgaag aggtaagagg ctttgcggaa tcagtgctta agacacagca   2460
aagattgctc gccaacaact acgtagagct tactgtagat gagatcgaag gtatctacag   2520
aagactctac tgatgatagc ataacccctt ggggcctcta aacgggtctt gaggggtttt   2580
ttgcccgctt ggtcgggccg cttcgcgagg gcccgttgac gacaacggtg cgatgggtcc   2640
cggcccgggt caagacgatg ccaatacgtt gcgacactac gccttggcac ttttagaatt   2700
gccttatcgt cctgataaga aatgtccgac cagctaaaga catcgcgtcc aatcaaagcc   2760
tagaaaatat aggcgaaggg acgctaataa gtctttcata agaccgcgca aatctaaaaa   2820
tatccttaga ttcacgatgc ggcacttcgg atgacttccg agcgagcctg gaacctcaga   2880
aaaacgtctg agagataccg cggatctcac acaggaaaca gctatgaaag ttacaaatca   2940
aaagaactaa aacaaaagc taaatgaatt gagagaagcg caaagaagt ttgcaaccta   3000 tactcaagag caagttgata aaattttttaa acaatgtgcc atcgccgcag ctaaagaaag   3060
aatcaacttg gctaaattgg cagtagaaga aacaggaatc ggtcttgtag aagataaaat   3120
tatcaaaaat cattttgcag cagaatatat ctacaataaa tataaaaatg aaaaaacttg   3180
```

```
tggcatcatc gaccatgacg attctttggg catcacaaag gttgctgaac caattggaat   3240
tgttgcagcc atcgttccta ctactaatcc aacttccaca gcaattttca aatcattgat   3300
ttctttgaaa acaagaaacg caatcttctt ttcaccacat ccacgtgcaa aaaaatctac   3360
aattgctgca gcaaaattaa ttttggatgc agctgttaaa gcaggagcac ctaaaaatat   3420
catcggctgg atcgatgagc catcaatcga actttctcaa gatttgatga gtgaagctga   3480
tatcatctta gcaacaggag gtccttcaat ggttaaagcg gcctattcat ctggaaaacc   3540
tgcaattggt gttggagcag gaaatacacc agcaatcatc gatgagagtg cagatatcga   3600
tatgcagta agctccatca tttttgtcaaa gacttatgac aatggagtaa tctgcgcttc   3660
tgaacaatca atcttggtta tgaattcaat ctacgaaaaa gttaagagg aatttgtaaa   3720
acgaggatca tatatcctca atcaaaatga aatcgctaaa atcaaagaaa ctatgtttaa   3780
aaatggagct attaatgctg acatcgttgg aaaatctgct tatatcattg ctaaaatggc   3840
aggaattgaa gttcctcaaa ctacaaagat cctatcggc gaagtacaat ctgttgaaaa   3900
aagcgagctg ttctcacatg aaaaactatc accagtactt gcaatgtata agttaagga   3960
ttttgatgaa gctctaaaaa aggcacaaag gctaatcgaa ttgggtggaa gtggacacac   4020
gtcatctttg tatatcgatt cacaaaacaa taaggataaa gttaaagaat tggattggc   4080
aatgaaaact tcaaggacat ttattaacat gccttcttca cagggagcaa gcggagattt   4140
gtacaatttt gcgatcgcac catcatttac tcttggatgc ggcacttggg gaggaaactc   4200
tgtatcgcaa aatgtagagc ctaaacattt gttgaatatt aaaagtgttg ctgaaagaag   4260
ggaaaatatg ctttggttta aagtgccaca aaaaatctat tttaaatatg gatgtcttag   4320
atttgcattg aaagaattga aagatatgaa taagaaaaga gcctttatcg taacagataa   4380
agatcttttt aaacttggat atgttaataa aatcacaaag gtactagatg agatcgatat   4440
taaatacagt atctttacag atattaaatc tgatccaact attgattcag taaaaaagg   4500
tgctaaagaa atgcttaact ttgaacctga tactatcatc tctattggtg gtggatcgcc   4560
aatggatgca gcaaaggtta tgcacttgtt gtatgaatat ccagaagcag aaattgaaaa   4620
tctagctatc aactttatgg atatcagaaa agagaatctgc aatttcccta aattgggtac   4680
aaaggcgatt tcagtagcta ttcctacaac tgctggtacc ggttcagagg caacacctttt   4740
tgcagttatc actaatgatg aaacaggaat gaaataccct ttgacttctt atgaattgac   4800
cccaaacatg gcaatcatcg atactgaatt gatgttgaat atgcctagaa aattgacagc   4860
agcaactgga atcgatgcat tggttcatgc tatcgaagca tatgtttcgg ttatggctac   4920
ggattatact gatgaattgg ccttgagagc aatcaaaatg atctttaaat atttgcctag   4980
agcctataaa aatgggacta acgacattga agcaagagaa aaaatggcac atgcctctaa   5040
tattgcgggg atggcatttg caaatgcttt cttgggtgta tgccattcaa tggctcataa   5100
acttggggca atgcatcacg ttccacatgg aattgcttgt gctgtattaa tcgaagaagt   5160
tattaaatat aacgctacag actgtccaac aaagcaaaca gcattccctc aatataaatc   5220
tcctaatgct aagagaaaat atgctgaaat tgcagagtat ttgaatttaa agggtactag   5280
cgataccgaa aaggtaacag ccttgatcga agctatttca aagttgaaga tcgatttgag   5340
tattccacaa aatatcagtg ccgctggaat caataaaaaa gatttttata atacgctaga   5400
taaaatgtca gagcttgctt ttgatgacca atgtacaaca gctaatccta ggtatccact   5460
tatcagtgaa cttaaggata tctatatcaa atcattttga tgattcttaa ataaacaata   5520
```

```
cttaaaacat tgaggaggt cttgtaaaca tggattggaa gaagatctat gaagacagaa    5580
catgcactgc agatgaagca gtaaagagca ttaagtcagg tgacagagtg ctatttgcgc    5640
actgtgttgc tgaaccgcca gttcttgtag aagcaatggt tgcgaatgca gctgcataca    5700
agaatgtaac ggtttcacac atggttaccc ttggaaaggg tgaatactca aaaccagaat    5760
ataaggaaaa ctttactttt gaaggttggt ttacaagccc ttcaacaaga ggatccattg    5820
cagaaggaca cggacagttt gtccctgtat tcttccacga ggtaccatct ttgatcagaa    5880
aagacatttt ccatgttgat gtattcatgg taatggtatc ccctccagat cataacggat    5940
tctgctgtgt gggtgtatct tctgactata cgatgcaggc tatcaaatca gcaaaaattg    6000
tacttgctga agtaaatgat caggtacctg tagtttatgg agatacattt gttcacgtta    6060
gtgaaatcga caagttcgta gaaacttcac atccacttcc agaaatcgga cttcctaaga    6120
tcggtgaagt agaagctgct attggtaagc actgcgcttc cctaatcgaa gatggttcca    6180
cattgcagct tggtatcgga gctattccgg atgctgtact ttcacagctt aaggacaaga    6240
aacaccttgg tatccactct gaaatgattt ccgacggtgt tgtagatctt tacgaagcag    6300
gcgttatcga ctgcagccaa aagtctatcg acaaaggcaa aatggcaatc acattcttga    6360
tgggaacgaa gagactttat gatttcgctg caaacaatcc aaaggttgaa ttgaagccgg    6420
ttgactacat caatcatcca tctgtagttg cacagtgctc caaaatggtt tgcatcaatg    6480
cttgcttgca agttgatttt atgggtcaga ttgtatccga tagtattggg acaaagcagt    6540
tctcaggagt aggcggtcag gttgacttcg taagaggtgc atccatgtct attgacggaa    6600
aaggtaaagc gatcatcgcg atgccttccg ttgcaaagaa gaaggatgga agtatgattt    6660
cgaagatcgt tccattcatc gatcacggtg cagctgtaac tacatccaga acgatgcgg    6720 actatgtcgt aacggaatat ggtattgctg aaatgaaggg taagtctttg caggacagag    6780
caagagcgtt gatcaatatt gcacaccctg atttcaaaga tgaattgaag gctgaatttg    6840
aaaagagatt caacgcggca ttctgatgat agcataaccc cttggggcct ctaaacgggt    6900 cttgagggt ttttgtcta ga                                              6922
```

<210> SEQ ID NO 11
<211> LENGTH: 9123
<212> TYPE: DNA
<213> ORGANISM: Artificial
<220> FEATURE:
<223> OTHER INFORMATION: Synthetic gene cluster for 1,4-BDO synthesis in
      Escherichia coli

<400> SEQUENCE: 11

```
ccatggcaaa cttttcatt ccaccagcca gcgtaattgg acgaggtgca gtaaaggaag      60
taggaacaag acttaagcaa attggagcta agaaagcgct tatcgttaca gatgcatttc     120
ttcatagcac aggtttatct gaagaagttg ctaaaaacat tcgtgaagct ggccttgatg     180
ttgcgatttt cccaaaagct caaccagatc agcagagata caagttcat gaaggtgtag      240 atgtattcaa acaagaaaac tgtgatgcac ttgtttctat cggtggaggt agctctcacg     300
atacagctaa agcaatcggt ttagttgcag caaacggcgg aagaatcaat gactatcaag     360
gtgtaaacag tgtagaaaaa ccagtcgttc cagtagttgc aatcactaca acagctggta     420
ctggtagtga acaacatctc ttgcagttta cagactc tgcacgtaaa gtaaaaatgc     480
ctgttattga tgagaaaatt actccaactg tagcaattgt tgacccagaa ttaatggtga     540
aaaaaccagc tggattaaca atcgcaactg gtatggacgc attatcacac gcaattgaag     600
```

-continued

```
catatgttgc aaaaggtgct acaccagtta ctgatgcatt tgcaattcaa gcaatgaaac    660
tcatcaatga atacttacca aaagcggtgg caaacggaga agacatcgaa gcacgtgaag    720
caatggctta tgcacaatac atggcaggag tggcatttaa caacggtggt ttaggattag    780
tacactctat ttctcaccaa gtaggtggag tttacaaatt acaacacgga atctgtaact    840
cagttaatat gccacacgtt tgcgcattca acctaattgc taaaactgag cgcttcgcac    900
acattgctga gcttttaggc gagaatgttt ctggcttaag cactgcagca gctgctgaga    960
gagcaattgt agcgcttgaa cgctataaca aaaacttcgg tatcccatct ggctatgcag   1020
aaatgggcgt gaaagaagag gatatcgaat tattagcgaa aaacgcattc gaagacgtat   1080
gtactcaaag caacccacgt gttgctacag ttcaagacat tgcacaaatc atcaaaaacg   1140
ctctgtaata attcttaaat aaacaatact taaaacattt gaggaggtct tgtaaacatg   1200
gcattgacac aaatggcatt agattcactg gatttcgacg caactgttgc gctggctgaa   1260
aaggtagctc cacacgttga cattcttgaa atcggtacac catgcatcaa gcacaacggt   1320
atcaagttgc tggaaactct gcgcgcaaag ttccctaaca acaagatcct ggttgacctg   1380
aagactatgg atgctggctt ctacgaagct gagcctttct acaaggctgg tgctgatatc   1440
actaccgttc tgggcgtagc tgatctgggt acaatcaaag gcgtaatcga cgctgctaac   1500
aagtacggca agaaggcaca gatcgacctg atcaatgttg gtgataaggc tgctcgtact   1560
aaggaagttg ctaagctggg cgcgcacatc attggcgttc acactggtct ggaccaacaa   1620
gctgctggtc aaactccttt gctgacctg gcaactgtaa ctggcctgaa cctgggtctg   1680
gaagtttccg tagctggtgg tgttaagcct gctactgttg cacaagttaa agacgctggt   1740
gctaccatca tcgtcgctgg cgctgctatc tacggtgctg ctgacccagc tgctgctgct   1800
gctgaaatca ctggcctggc taagtaataa ttcttaaata aacaatactt aaaacatttg   1860
aggaggtctt gtaaacatga acaaatatca agagctcgtg gtcagcaagc tgaccaatgt   1920
tatcaataac actgcagaag gctatgacga caagattttg agtctagtcg atgcagccgg   1980
ccgtacattt atcggtggtg ctggccgttc cttgctggtt tcccgtttct ttgcaatgcg   2040
cttggtgcat gcaggttacc aagttagcat ggtcggtgaa gttgttactc caagtatcca   2100
agctggtgat cttttcattg tgatctctgg ctctggcagc acagaaaccc tgatgccttt   2160
ggttaagaag gcaaagagcc aaggtgccaa gattatcgtg atttccatga aggctcagtc   2220
cccaatggct gaattggctg atctggttgt gccagttggt ggcaacgatg ccaatgcatt   2280
tgacaagact catggtatgc ctatgggtac tattttcgag ttgtccaccc tgtggttcct   2340
cgaagcgact attgccaagc tggtagatca aaaaggtctg acagaagaag gtatgcgcgc   2400
gattcatgct aacctcgagt aataatagca taacccttg gggcctctaa acgggtcttg   2460
aggggttttt tgtgttgaca attaatcatc cggctcgtat aatgtgtgga attgtgagcg   2520
gataacaatt tcacacagga aacagaccat gagtaatgaa gtatctataa agaattaat    2580
tgaaaaggca aaggtggcac aaaaaaaatt ggaagcctat agtcaagaac aagttgatgt   2640
actagtaaaa gcactaggaa aagtggttta tgataatgca gaaatgtttg caaagaagc    2700
agttgaagaa acagaaatgg gtgtttatga agataaagta gctaaatgtc atttgaaatc   2760
aggagctatt tggaatcata taaaagacaa gaaaactgta ggcataataa agaagaacc    2820
tgaaagggca cttgttatg ttgctaagcc aaagggagtt gtggcagcta ctacgcctat   2880
aactaatcca gtggtaactc ctatgtgtaa tgcaatggct gctataaagg cagaaatac    2940
aataatagta gcaccacatc ctaaagcaaa gaaagtttca gctcatactg tagaacttat   3000
```

```
gaatgctgag cttaaaaaat tgggagcacc agaaaatatc atacagatag tagaagcacc   3060
atcaagagaa gctgctaagg aacttatgga aagtgctgat gtagttattg ctacaggcgg   3120
tgctggaaga gttaaagctg cttactccag tggaagacca gcttatggcg ttggacctgg   3180
aaattcacag gtaatagttg ataagggata cgattataac aaagctgcac aggatataat   3240
aacaggaaga aaatatgaca atggaattat atgttcttca gagcaatcag ttatagctcc   3300
tgctgaagat tatgataagg taatagcagc ttttgtagaa aatggggcat tctatgtaga   3360
agatgaggaa acagtagaaa agtttagatc aactttattt aaagatggaa aaataaacag   3420
caagattata ggtaaatccg tccaaattat tgcggatctt gcaggagtaa aagtaccaga   3480
aggtactaag gttatagtac ttaagggtaa aggtgcagga gaaaaagatg tactttgtaa   3540
agaaaaaatg tgtccagttt tagtagcatt gaaatatgat acttttgaag aagcagttga   3600
aatagctatg gctaattata tgtatgaagg agctggtcat acagcaggca tacattctga   3660
caatgacgag aacataagat atgcaggaac tgtattacct ataagcagat tagttgtaaa   3720
tcagcctgca actactgctg aggaagtttt caataatgga tttaacccta ctactacact   3780
aggctgcgga tcatggggca gaaacagtat ttcagaaaat cttacttacg agcatcttat   3840
aaatgtttca agaatagggt atttcaataa agaagcaaaa gttcctagct atgaggaaat   3900
atggggataa taattcttaa ataaacaata cttaaaacat ttgaggaggt cttgtaaaca   3960
tgcaactttt caaactcaag agtgtaacac atcactttga cacttttgca gaatttgcca   4020
aggaattctg tcttggagaa cgcgacttgg taattaccaa cgagttcatc tatgaaccgt   4080
atatgaaggc atgccagctc ccctgccatt ttgttatgca ggagaaatat gggcaaggcg   4140
agccttctga cgaaatgatg aataacatct tggcagacat ccgtaatatc cagttcgacc   4200
gcgtaatcgg tatcggagga ggtacggtta ttgacatctc taaacttttc gttctgaaag   4260
gattaaatga tgtactcgat gcattcgacc gcaaaatacc tcttatcaaa gagaaagaac   4320
tgatcattgt gcccacaaca tgcggaacgg gtagcgaggt gacgaacatt tctatcgcag   4380
aaatcaaaag ccgtcacacc aaaatgggat tggctgacga tgccattgtt gcagaccatg   4440
ccatcatcat acctgaactt ctgaagagct tgccttttcca cttctacgca tgcagtgcaa   4500
tcgatgctct tatccatgcc atcgagtcat acgtatctcc taaagccagt ccatattctc   4560
gtctgttcag tgaggcggct tgggacatta tcctggaagt attcaagaaa atcgccgaac   4620
acggccctga ataccgcttc gaaaagctgg gagaaatgat catggccagc aactatgccg   4680
gtatagcctt cggaaatgca ggagtaggag ccgtccacgc actatcctac ccgttgggag   4740
gcaactatca cgtgccgcat ggagaagcaa actatcagtt cttcacagag gtattcaaag   4800
tataccaaaa gaagaatcct ttcggctata tagtcgaact caactggaag ctctccaaga   4860
tactgaactg ccagcccgaa tacgtatatc cgaagctgga tgaacttctc ggatgccttc   4920
ttaccaagaa acctttgcac gaatacggca tgaaggacga agaggtaaga ggctttgcgg   4980
aatcagtgct taagacacag caaagattgc tcgccaacaa ctacgtagag cttactgtag   5040
atgagatcga aggtatctac agaagactct actaataatt cttaaataaa caatacttaa   5100
aacatttgag gaggtcttgt aaacatgaaa gttacaaatc aaaagaaact aaaacaaaag   5160
ctaaatgaat tgagagaagc gcaaaagaag tttgcaacct atactcaaga gcaagttgat   5220 aaaatttttta aacaatgtgc catagccgca gctaaagaaa gaataaactt agctaaatta   5280
gcagtagaag aaacaggaat aggtcttgta gaagataaaa ttataaaaaa tcattttgca   5340
```

-continued

```
gcagaatata tatacaataa atataaaaat gaaaaaactt gtggcataat agaccatgac      5400
gattctttag gcataacaaa ggttgctgaa ccaattggaa ttgttgcagc catagttcct      5460
actactaatc caacttccac agcaattttc aaatcattaa tttctttaaa aacaagaaac      5520
gcaatattct tttcaccaca tccacgtgca aaaaaatcta caattgctgc agcaaaatta      5580
attttagatg cagctgttaa agcaggagca cctaaaaata taataggctg gatagatgag      5640
ccatcaatag aactttctca agatttgatg agtgaagctg atataatatt agcaacagga      5700
ggtccttcaa tggttaaagc ggcctattca tctggaaaac ctgcaattgg tgttggagca      5760
ggaaatacac cagcaataat agatgagagt gcagatatag atatggcagt aagctccata      5820
attttatcaa agacttatga caatggagta atatgcgctt ctgaacaatc aatattagtt      5880
atgaattcaa tatcgaaaaa agttaaagag gaatttgtaa aacgaggatc atatatactc      5940
aatcaaaatg aaatagctaa aataaaagaa actatgttta aaaatggagc tattaatgct      6000
gacatagttg gaaatctgc ttatataatt gctaaaatgg caggaattga agttcctcaa       6060
actacaaaga tacttatagg cgaagtacaa tctgttgaaa aaagcgagct gttctcacat      6120
gaaaaactat caccagtact tgcaatgtat aaagttaagg attttgatga agctctaaaa      6180
aaggcacaaa ggctaataga attaggtgga agtggacaca cgtcatcttt atatatagat      6240
tcacaaaaca ataaggataa agttaaagaa tttggattag caatgaaaac ttcaaggaca      6300
tttattaaca tgccttcttc acagggagca agcggagatt tatacaattt tgcgatagca      6360
ccatcattta ctcttggatg cggcacttgg ggaggaaact ctgtatcgca aaatgtagag      6420
cctaaacatt tattaaatat taaaagtgtt gctgaaagaa gggaaaatat gctttggttt      6480
aaagtgccac aaaaaatata ttttaaatat ggatgtctta gatttgcatt aaaagaatta      6540
aaagatatga ataagaaaag agcctttata gtaacagata aagatctttt taaacttgga      6600
tatgttaata aaataacaaa ggtactagat gagatagata ttaaatacag tatatttaca      6660
gatattaaat ctgatccaac tattgattca gtaaaaaaag gtgctaaaga aatgcttaac      6720
tttgaacctg atactataat ctctattggt ggtggatcgc caatggatgc agcaaaggtt      6780
atgcacttgt tatatgaata tccagaagca gaaattgaaa atctagctat aaactttatg      6840
gatataagaa agagaatatg caatttccct aaattaggta caaaggcgat ttcagtagct      6900
attcctacaa ctgctggtac cggttcagag gcaacaccct ttgcagttat aactaatgat      6960
gaaacaggaa tgaaataccc tttaacttct tatgaattga ccccaaacat ggcaataata      7020
gatactgaat taatgttaaa tatgcctaga aaattaacag cagcaactgg aatagatgca      7080
ttagttcatg ctatagaagc atatgtttcg gttatggcta cggattatac tgatgaatta      7140
gccttaagag caataaaaat gatatttaaa tatttgccta gagcctataa aaatgggact      7200
aacgacattg aagcaagaga aaaaatggca catgcctcta atattgcggg gatggcattt      7260
gcaaatgctt tcttaggtgt atgccattca atggctcata acttggggc aatgcatcac      7320 gttccacatg gaattgcttg tgctgtatta atagaagaag ttattaaata taacgctaca      7380
gactgtccaa caaagcaaac agcattccct caatataaat ctcctaatgc taagagaaaa      7440
tatgctgaaa ttgcagagta tttgaattta aagggtacta gcgataccga aaaggtaaca      7500
gccttaatag aagctatttc aaagttaaag atagatttga gtattccaca aaatataagt      7560
gccgctggaa taaataaaaa agattttat aatacgctag ataaaatgtc agagcttgct       7620
tttgatgacc aatgtacaac agctaatcct aggtatccac ttataagtga acttaaggat      7680
atctatataa aatcatttta ataattctta aataaacaat acttaaaaca tttgaggagg      7740
```

```
tcttgtaaac atggattgga agaagatcta tgaagacaga acatgcactg cagatgaagc    7800
agtaaagagc attaagtcag gtgacagagt gctatttgcg cactgtgttg ctgaaccgcc    7860
agttcttgta gaagcaatgg ttgcgaatgc agctgcatac aagaatgtaa cggtttcaca    7920
catggttacc cttggaaagg gtgaatactc aaaaccagaa tataaggaaa actttacttt    7980
tgaaggttgg tttacaagcc cttcaacaag aggatccatt gcagaaggac acggacagtt    8040
tgtccctgta ttcttccacg aggtaccatc tttaatcaga aaagacattt tccatgttga    8100
tgtattcatg gtaatggtat cccctccaga tcataacgga ttctgctgtg tgggtgtatc    8160
ttctgactat acgatgcagg ctatcaaatc agcaaaaatt gtacttgctg aagtaaatga    8220
tcaggtacct gtagtttatg gagatacatt tgttcacgtt agtgaaatcg acaagttcgt    8280
agaaacttca catccacttc cagaaatcgg acttcctaag atcggtgaag tagaagctgc    8340
tattggtaag cactgcgctt ccctaatcga agatggttcc acattacagc ttggtatcgg    8400
agctattccg gatgctgtac tttcacagct taaggacaag aaacaccttg gtatccactc    8460
tgaaatgatt tccgacggtg ttgtagatct ttacgaagca ggcgttatag actgcagcca    8520
aaagtctatc gacaaaggca aaatggcaat aacattctta atgggaacga agagacttta    8580
tgatttcgct gcaaacaatc caaggttga attaaagccg gttgactaca taaatcatcc    8640
atctgtagtt gcacagtgct ccaaaatggt ttgcatcaat gcttgcttgc aagttgattt    8700
tatgggtcag attgtatccg atagtattgg gacaaagcag ttctcaggag taggcggtca    8760
ggttgacttc gtaagaggtg catccatgtc tattgacgga aaaggtaaag cgatcatcgc    8820
gatgccttcc gttgcaaaga agaaggatgg aagtatgatt tcgaagatcg ttccattcat    8880
cgatcacggt gcagctgtaa ctacatccag aaacgatgcg gactatgtcg taacggaata    8940
tggtattgct gaaatgaagg gtaagtcttt acaggacaga gcaagagcgt taatcaatat    9000
tgcacaccct gatttcaaag atgaattaaa ggctgaattt gaaaagagat caacgcggc    9060 attctaataa tagcataacc ccttggggcc tctaaacggg tcttgagggg tttttgaag    9120 ctt                                                                  9123
```